(12) United States Patent
Horcajadas et al.

(10) Patent No.: US 12,181,462 B2
(45) Date of Patent: Dec. 31, 2024

(54) IDENTIFICATION OF VIABLE HUMAN EMBRYOS

(71) Applicant: Overture Life, Inc., New York, NY (US)

(72) Inventors: José A. Horcajadas, Alconbendas (ES); Hussain A. Abdulla, Corpus Christi, TX (US)

(73) Assignee: Overture Life, Inc., New York, NY (US)

( * ) Notice: Subject to any disclaimer, the term of this patent is extended or adjusted under 35 U.S.C. 154(b) by 212 days.

(21) Appl. No.: 16/937,692

(22) Filed: Jul. 24, 2020

(65) Prior Publication Data
US 2021/0025868 A1    Jan. 28, 2021

Related U.S. Application Data

(60) Provisional application No. 62/878,524, filed on Jul. 25, 2019.

(51) Int. Cl.
*G01N 33/50* (2006.01)

(52) U.S. Cl.
CPC ............... *G01N 33/5005* (2013.01)

(58) Field of Classification Search
CPC ............. G01N 33/5005; G01N 33/689
See application file for complete search history.

(56) References Cited

U.S. PATENT DOCUMENTS

| | | | |
|---|---|---|---|
| 7,723,289 B2 | 5/2010 | Barnea | |
| 7,981,399 B2 | 7/2011 | Burns | |
| 8,486,690 B2 | 7/2013 | Burns | |
| 8,721,521 B2 | 5/2014 | Wong et al. | |
| 8,754,014 B2 | 6/2014 | Hamamah et al. | |
| 8,969,017 B2 | 3/2015 | Mickiewicz et al. | |
| 8,989,475 B2 | 3/2015 | Wong et al. | |
| 9,090,938 B2 | 7/2015 | Hamamah et al. | |
| 9,121,066 B2 | 9/2015 | Hamamah et al. | |
| 9,228,931 B2 | 1/2016 | Wong et al. | |
| 9,262,582 B2 | 2/2016 | Kenny et al. | |
| 9,348,972 B2 | 5/2016 | Yao | |
| 9,354,244 B2 | 5/2016 | Yamashita et al. | |

(Continued)

FOREIGN PATENT DOCUMENTS

| CA | 1055370 A | 5/1979 |
|---|---|---|
| EP | 2400303 A1 | 12/2011 |

(Continued)

OTHER PUBLICATIONS

Hendrikx, T., and B. Schnabl. "Indoles: metabolites produced by intestinal bacteria capable of controlling liver disease manifestation." Journal of internal medicine 286.1 (2019): 32-40. (Year: 2019).*

(Continued)

*Primary Examiner* — Louise W Humphrey
*Assistant Examiner* — Candice Lee Swift
(74) *Attorney, Agent, or Firm* — DZ Buschmann Law

(57) ABSTRACT

Disclosed herein is a method for assessing the probability of embryo implantation success during the in vitro fertilization process. A method of the disclosure can predict embryo implantation success based on, for example, the amount of specific metabolites present in embryo conditioned culture media.

44 Claims, 3 Drawing Sheets

(56) References Cited

U.S. PATENT DOCUMENTS

| | | |
|---|---|---|
| 9,410,939 B2 | 8/2016 | Zernicka-Goetz et al. |
| 9,482,659 B2 | 11/2016 | Loewke et al. |
| 9,499,778 B2 | 11/2016 | Palermo |
| 9,664,692 B2 | 5/2017 | Ledee et al. |
| 9,879,307 B2 | 1/2018 | Chavez et al. |
| 9,984,278 B2 | 5/2018 | Needleman et al. |
| 10,059,994 B2 | 8/2018 | Hamamah et al. |
| 2007/0162992 A1 | 7/2007 | Burns |
| 2009/0215085 A1 | 8/2009 | Oehninger et al. |
| 2010/0099135 A1 | 4/2010 | Katz-Jaffe et al. |
| 2011/0195427 A1 | 8/2011 | Selinfreund et al. |
| 2011/0236922 A1 | 9/2011 | Burns |
| 2012/0123193 A1 | 5/2012 | Posillico et al. |
| 2012/0277180 A1 | 11/2012 | Marini et al. |
| 2014/0221236 A1 | 8/2014 | Borowski et al. |
| 2018/0180618 A1 | 6/2018 | Bux et al. |
| 2018/0214068 A1 | 8/2018 | Munne et al. |
| 2018/0303798 A1 | 10/2018 | Maxia |

FOREIGN PATENT DOCUMENTS

| | | |
|---|---|---|
| EP | 2975402 A1 | 1/2016 |
| WO | WO-2009059139 A1 | 5/2009 |
| WO | WO-2011008932 A1 | 1/2011 |
| WO | WO-2011080170 A1 | 7/2011 |
| WO | WO-2013142408 A1 | 9/2013 |
| WO | WO-2015001458 A1 | 1/2015 |
| WO | WO-2015022541 A1 | 2/2015 |
| WO | WO-2017081473 A1 | 5/2017 |
| WO | WO-2018053247 A1 | 3/2018 |

OTHER PUBLICATIONS

Russel J. Reiter, Dun-Xian Tan, Hiroshi Tamura, Maria Helena C. Cruz & Lorena Fuentes-Broto (2014) Clinical relevance of melatonin in ovarian and placental physiology: a review, Gynecological Endocrinology, 30:2, 83-89, DOI: 10.3109/09513590.2013.849238 (Year: 2014).*

James D. Adams, Mikel C. Heins, Garold S. Yost, 3-methylindole inhibits lipid peroxidation, Biochemical and Biophysical Research Communications, vol. 149, Issue 1, (Year: 1987).*

Sigma-Aldrich, https://www.sigmaaldrich.com/US/en/product/aldrich/w301912, accessed Aug. 4, 2022 (Year: 2022).*

Toxicity of 8-hydroxyquinoline on embryos and larvae of Paramisgurnus dabryanus (P. dabryanus) By: Wu, Xiaohua; Dang, Bingjun; Du, Qiyan; Chang, Zhongjie Zhongguo Gonggong Weisheng (2010), 26(8), 993-99 (Year: 2010).*

Rødgaard, Tina, Peter MH Heegaard, and Henrik Callesen. "Non-invasive assessment of in-vitro embryo quality to improve transfer success." Reproductive biomedicine online 31.5 (2015): 585-592. (Year: 2015).*

M. Sargent (Ed.), Guide to achieving reliable quantitative LC-MS measurements, RSC Analytical Methods Committee, 2013. ISBN 978-0-948926-27-3. (Year: 2016).*

Mohammadi, Somayeh, et al. "Toxic compounds from tobacco in placenta samples analyzed by UPLC-QTOF-MS." Journal of Pharmaceutical and Biomedical Analysis 145 (2017): 331-338. (Year: 2017).*

Iles, Ray K., et al. "Secretome profile selection of optimal IVF embryos by matrix-assisted laser desorption ionization time-of-flight mass spectrometry." Journal of assisted reproduction and genetics 36.6 (2019): 1153-1160. (Year: 2019).*

HMDB, 3-Amino-1-hydroxy-5,7-dimethyl-adamantane; https://hmdb.ca/metabolites/HMDB0060738; accessed Mar. 13, 2023 (Year: 2023).*

Pubchem-Tecostamine; https://pubchem.ncbi.nlm.nih.gov/compound/120773; accessed on Mar. 15, 2023 (Year: 2005).*

Bakr, Riham Omar, et al. "Tecoma stans: Alkaloid profile and antimicrobial activity." Journal of Pharmacy & Bioallied Sciences 11.4 (2019): 341. (Year: 2019).*

Pubchem-Dasytrichone; https://pubchem.ncbi.nlm.nih.gov/compound/442586; accessed Mar. 15, 2023 (Year: 2005).*

Dasytrichone, no result in HMDB; https://hmdb.ca/unearth/q?utf8=%E2%9C%93&query=Dasytrichone+&searcher=metabolites&button=; accessed Mar. 15, 2023 (Year: 2023).*

HMDB, (2,7-Dimethyloctahydro-1Hcyclopenta[c]pyridin-4-yl)methanol; a/unearth/q?utf8=%E2%9C%93&query=%282%2C7-Dimethyloctahydro-1 Hcyclopenta%5Bc%5Dpyridin-4-yl%29methanol&searcher=metabolites&button=; accessed Mar. 15, 2023 (Year: 2023).*

Stone, Trevor W. "Tryptophan and kynurenines: continuing to court controversy." Clinical Science 130.15 (2016): 1335-1337. (Year: 2016).*

Badawy, Abdulla A-B., Aryan MA Namboodiri, and John R. Moffett. "The end of the road for the tryptophan depletion concept in pregnancy and infection." Clinical Science 130.15 (2016): 1327-1333. (Year: 2016).*

KEGG1; https://www.genome.jp/entry/C00328; accessed Jul. 25, 2023 (Year: 2023).*

KEGG2; https://www.genome.jp/entry/C00078; accessed Jul. 23, 2023 (Year: 2023).*

University of Missouri Mass Spectrometry Facility; https://msfacility.missouri.edu/calculating.html; accessed Jul. 23, 2023 (Year: 2019).*

Niu, Tian-Tian, et al. "Interaction between kynurenine and Aryl hydrocarbon receptor in regulating the balance of T helper 17 cells and regulatory T-cells in decidua during early gestation." Reproductive and Developmental Medicine 2.01 (2018): 8-14. (Year: 2018).*

Ng SW, Norwitz GA, Pavlicev M, Tilburgs T, Simon C, Norwitz ER. Endometrial Decidualization: The Primary Driver of Pregnancy Health. Int J Mol Sci. Jun. 8, 2020;21(11):4092. doi: 10.3390/ijms21114092. PMID: 32521725; PMCID: PMC7312091. (Year: 2020).*

Borges Jr., Edson et al., Non-invasive prediction of blastocyst implantation, ongoing preg-nancy and live birth, by mass spectrometry lipid fingerprinting, JBRA Assisted Reproduction 2016;20(4):227-231 doi: 10.5935/1518-0557.20160044.

Brison, Daniel R et al., Predicting human embryo viability: the road to non-invasive analysis of the secretome using metabolic footprinting,— vol. 15. No 3. 2007 296-302 Reproductive BioMedicine Online; http://www.rbmonline.com/Article/2892 on web Jul. 16, 2007.

Enquobahrie, Daniel A et al. Maternal Early Pregnancy Serum Metabolites and Risk of Gestational Diabetes Mellitus. The Journal of clinical endocrinology and metabolism vol. 100,11(2015): 4348-56. doi:10.1210/jc.2015-2862.

Fu, Jing et al., Non-invasive metabolomic profiling of Day 3 embryo culture media using near-infrared spectroscopy to assess the development potential of embryos, Acta Biochim Biophys Sin 2013, 45: 1074-1078 |.

Ftukijwatari, T et al., Changes in the urinary excretion of the metabolites of the tryptophan-niacin pathway during pregnancy in Japanese women and rats, J Nutr Sci Vitaminol (Tokyo).Dec. 2004;50(6):392-8.

Hardarson, T et al., Non-invasive metabolomic profiling of Day 2 and 5 embryo culture medium: a prospective randomized trial, Human Reproduction, vol. 27, No. 1 pp. 89-96, 2012, Advanced Access publication on Nov. 7, 2011 doi: 10.1093/humrep/der373.

Li, Xiong et al., Non-invasive metabolomic profiling of embryo culture media and morphology grading to predict implantation outcome in frozen-thawed embryo transfer cycles, J Assist Reprod Genet, 2015, 32:1597-1605 , DOI 10.1007/s10815-015-0578-z.

Montsko, G et al., Non-Invasive Assessment of the Embryo Viability via the Analysis of the Culture Media, InTech, Chapter 6, 2017, pp. 80-95, http://dx.doi.org/10.5772/intechopen.69436.

Nagy, ZP et al., Symposium: Innovative techniques in human embryo viability assessment, Non-invasive assessment of embryo viability by metabolomic profiling of culture media('metabolomics'), RBM Online—vol. 17. No 4. 2008 502-507 Reproductive Bio Medicine Online; www.rbmonline.com/Article/3609 on web Aug. 13, 2008.

Nilsen, Roy M et al., Maternal Tryptophan and Kynurenine Pathway Metabolites and Risk of Preeclampsia, Obstet Gynecol. Jun. 2012, 119(6): 1243-1250, doi: 10.1097/AOG.0b013e318255004e.

(56) References Cited

OTHER PUBLICATIONS

Oehninger, Sergio, Noninvasive Methods of Embryo Selection, Reproductomics, pp. 209-225, https://doi.org/10.1016/B978-0-12-812571-7.00013-7.

Rødgaard, Tina et al., Non-invasive assessment of in-vitro embryo quality to improve transfer success, Reproductive BioMedicine Online, 2015, 31, 585-592.

Rose, M.D., Ph.D., David P. et al., Excretion of tryptophan metabolites as affected by pregnancy, contraceptive steroids, and steroid hormones, The American Journal of Clinical Nutrition 24: Jun. 1971, pp. 673-683.

Seli, M.D., Emre et al., Noninvasive metabolomic profiling of embryo culture media using Raman and near-infrared spectroscopy correlates with reproductive potential of embryos in women undergoing in vitro fertilization, Fertility and Sterility, vol. 88, No. 5, Nov. 2007, pp. 1350-1357.

Shibata, K et al., Urinary excretion levels of water-soluble vitamins in pregnant and lactating women in Japan, J Nutr Sci Vitaminol (Tokyo). 2013;59(3):178-86.

T. Hardarson, et al., Non-invasive metabolomic profiling of Day 2 and 5 embryo culture medium: a prospective randomized trial, Human Reproduction, vol. 27, No. 1 pp. 89-96, 2012.

Uyar, PhD, Asli et al., Metabolomic Assessment of Embryo Viability, Semin Reprod Med. Mar. 2014 ; 32(2): 141-152.doi:10.1055/s-0033-1363556.

Zhang, Yan-Li et al., Non-invasive assessment of culture media from goat cloned embryos associated with subjective morphology by gas chromatography—mass spectroscopy-based metabolomic analysis, Animal Science Journal, 2017, pp. 1-11, doi:10.1111/asj.12885.

Ahlström A, Wikland M, Rogberg L, Barnett JS, Tucker M, Hardarson T. Cross-validation and predictive value of near-Infrared spectroscopy algorithms for day-5 blastocyst transfer. Reprod Biomed Online 2011;22:477-84.

Bracewell-Milnes T, Saso S, Abdalla H, Nikolau D, Norman-Taylor J, Johnson M, et al. Metabolomics as a tool to identify biomarkers to predict and improve outcomes in reproductive medicine: a systematic review. Hum Reprod Update 2017;23:1-14.

D'Alessandro A, Federica G, Palini S, Bulletti C, Zolla L. A mass spectrometry-based targeted metabolomics strategy of human blastocoele fluid: a promising tool in fertility research. Molecular BioSystems 2012;8:953-8.

Pudakalakatti, S.M., Uppangala S, D'Souza F, Kalthur G, Kumar P, Adiga SK et al. NMR studies of preimplantation embryo metabolism in human assisted reproductive techniques: a new biomarker for assessment of embryo implantation potential. NMR in Biomedicine 2013;26:20-27.

Seli E, Bruce C, Botros L, Henson M, Roos P, Judge K et al. Receiver operating characteristic (ROC) analysis of day 5 morphology grading and metabolomic Viability Score on predicting implantation outcome. J Assist Reprod Genet 2011;28:137-44.

Berdy, J., et al. "Metabolites of gentamicin-producing *Micromonospora* species I. Isolation and identification of metabolites." The Journal of antibiotics 30.11 (1977): 945-954.

Blaženović, I., Kind, T., Sa, M. R., Ji, J., Vaniya, A., Wancewicz, B., . . . & Fiehn, O. (2019). Structure annotation of all mass spectra in untargeted metabolomics. Analytical chemistry, 91(3), 2155-2162.

Morbeck, D. E., Krisher, R. L., Herrick, J. R., Baumann, N. A., Matern, D., & Moyer, T. (2014). Composition of commercial media used for human embryo culture. Fertility and Sterility, 102(3), 759-766.

Truong, T. and Gardner, D.K. (2017). Antioxidants improve IVF outcome and subsequent embryo development in the mouse. Human Reproduction, 32(12), pp. 2404-2413.

Vitrolife G1TM Plus product description at https://www.vitrolife.com/products/ivf-media-oil/g-1/ retrieved Jun. 20, 2023.

Vitrolife G1TM Plus Product Insert REF 26080, version 08 at https://www.vitrolife.com/products/ivf-media--oil/g-1/ retrieved Jun. 20, 2023.

Wolf, S., Schmidt, S., Müller-Hannemann, M., & Neumann, S. (2010). In silico fragmentation for computer assisted identification of metabolite mass spectra. BMC bioinformatics, 11, 1-12.

Yasuno, R. and Wada, H. (1998). Biosynthesis of lipoic acid in *Arabidopsis*: cloning and characterization of the cDNA for lipoic acid synthase. Plant physiology, 118(3), pp. 935-943.

Extended European Search Report dated Jul. 7, 2023 in EP20845130.2.

Krisher, Rebecca L., William B. Schoolcraft, and Mandy G. Katz-Jaffe. "Omics as a window to view embryo viability." Fertility and Sterility 103.2 (2015): 333-341.

Barca, et al., "Targeted metabolomics reveals reduced levels of polyunsaturated choline plasmalogens and a smaller dimethylarginine/arginine ratio in the follicular fluid of patients with a diminished ovarian reserve" Human Reproduction (2017) vol. 32, pp. 2269-2278.

* cited by examiner

IDENTIFICATION OF VIABLE HUMAN EMBRYOS

CROSS-REFERENCE

This application claims the benefit of U.S. Provisional Application No. 62/878,524, filed Jul. 25, 2019, the content of which is incorporated herein by reference in its entirety.

BACKGROUND

Assisted reproductive technologies (ARTs) such as in vitro fertilization (IVF) provide infertile couples with an opportunity to achieve a pregnancy. Today, over 1% of all infants born in the United States and up to 5-8% born in some European countries are conceived using ART.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the disclosure provides a method comprising: a) measuring an amount of a metabolite in a sample of culture media in which an embryo has been cultured in vitro, wherein the metabolite is caprolactam, N-cyclohexylformamide, threo-3-hydroxy-2-methylbutyric acid, sulfoacetic acid, (2,7-dimethyloctahydro-1H-cyclopenta[c]pyridin-4-yl)methanol, trans-3-indoleacrylic acid, pantothenic acid, diaveridine, (5-benzyl-3,6-dioxo-2-piperazinyl)acetic acid, dasytrichone, indole, leucoline, skatole, 6-hydroxycaproic acid, 1,2,6-hexanetriol, naphthalen-2-amine, 8-hydroxyquinoline, 2,2,6,6-tetramethyl-4-piperidinol, 1,5-naphthalenediamine, 1H-indole-2-carboxylic acid, (E)-dacarbazine, dinitrosopentamethylenetetramine, 5-hydroxyindole-3-acetic acid, 3-amino-5,7-dimethyl-1-adamantanol, 11-aminoundecanoic acid, kynurenine, N-hydroxy-L-tryptophan, 2-(methylamino)-1H-benzo[de]isoquinoline-1,3(2H)-dione, 5-hydroxy-N-formylkynurenine, or N-lauroylglycine; and b) assessing a likelihood of success of implantation of the embryo into a uterus upon introduction of the embryo into the uterus based at least partially on the amount of the metabolite present in the sample of culture media.

In some embodiments, the disclosure provides a method comprising measuring an amount of each of a plurality of metabolites in a mixture, wherein the metabolites is (2,7-dimethyloctahydro-1H-cyclopenta[c]pyridin-4-yl)methanol, trans-3-indoleacrylic acid, pantothenic acid, diaveridine, (5-benzyl-3,6-dioxo-2-piperazinyl)acetic acid, dasytrichone, indole, skatole, 8-hydroxyquinoline, (E)-dacarbazine, kynurenine, or N-hydroxy-L-tryptophan.

In some embodiments, the disclosure provides a method comprising: a) performing an assay to obtain a first set of mass spectra corresponding to a first metabolite present in a sample of culture media in which an embryo has been cultured in vitro ($ms_1$); b) using the first set of mass spectra to determine an amount of the first metabolite in the sample of culture media, wherein the amount of the first metabolite is associated with a low probability of embryo implantation success; c) performing an assay to obtain a second set of mass spectra corresponding to a second metabolite present in the sample of culture media in which the embryo has been cultured in vitro ($ms_2$); d) using the second set of mass spectra to determine an amount of the second metabolite, wherein the amount of the second metabolite is associated with a high probability of embryo implantation success; and e) comparing the amount of the first metabolite with the amount of the second metabolite.

In some embodiments, the disclosure provides a method comprising: a) measuring an amount of each of four metabolites in a sample of culture media in which an embryo has been cultured in vitro; and b) assessing a likelihood of success of implantation of the embryo into a uterus upon introduction of the embryo into the uterus based on the amount of the 4 metabolites in the sample of culture media, wherein: i) the amount of at least one of the metabolites in the sample of culture media is associated with a low probability of embryo implantation success; and ii) the amount of at least one of the metabolites in the sample of culture media is associated with a high probability of implantation success.

In some embodiments, the disclosure provides a method comprising a) requesting an assay on a sample of culture media in which an embryo has been cultured in vitro, b) receiving a communication, wherein the communication assesses a likelihood of success of implantation of the embryo into a uterus upon introduction of the embryo into the uterus based on an amount of one or more metabolites measured in the sample of culture media; and c) transferring the embryo into a subject's uterus, wherein: i) the communication states that the likelihood of success of implantation of the embryo into the uterus is high; and ii) one of the metabolites measured in the sample of culture media is caprolactam, N-cyclohexylformamide, threo-3-hydroxy-2-methylbutyric acid, sulfoacetic acid, (2,7-dimethyloctahydro-1H-cyclopenta[c]pyridin-4-yl)methanol, trans-3-indoleacrylic acid, pantothenic acid, diaveridine, (5-benzyl-3,6-dioxo-2-piperazinyl)acetic acid, dasytrichone, indole, leucoline, skatole, 6-hydroxycaproic acid, 1,2,6-hexanetriol, naphthalen-2-amine, 8-hydroxyquinoline, 2,2,6,6-tetramethyl-4-piperidinol, 1,5-naphthalenediamine, 1H-indole-2-carboxylic acid, (E)-dacarbazine, dinitrosopentamethylenetetramine, 5-hydroxyindole-3-acetic acid, 3-amino-5,7-dimethyl-1-adamantanol, 11-aminoundecanoic acid, kynurenine, N-hydroxy-L-tryptophan, 2-(methylamino)-1H-benzo[de]isoquinoline-1,3(2H)-dione, 5-hydroxy-N-formylkynurenine, or N-lauroylglycine.

In some embodiments, the disclosure provides a kit comprising an aliquot of each of 3 of the following compounds: caprolactam, N-cyclohexylformamide, threo-3-Hydroxy-2-methylbutyric acid, sulfoacetic acid, (2,7-Dimethyloctahydro-1H-cyclopenta[c]pyridin-4-yl)methanol, trans-3-indoleacrylic acid, pantothenic acid, diaveridine, (5-benzyl-3,6-dioxo-2-piperazinyl)acetic acid, dasytrichone, indole, leucoline, skatole, 6-hydroxycaproic acid, 1,2,6-hexanetriol, naphthalen-2-amine, 8-hydroxyquinoline, 2,2,6,6-tetramethyl-4-piperidinol, 1,5-naphthalenediamine, 1H-indole-2-carboxylic acid, (E)-dacarbazine, dinitrosopentamethylenetetramine, 5-hydroxyindole-3-acetic acid, 3-amino-5,7-dimethyl-1-adamantanol, 11-aminoundecanoic acid, kynurenine, N-hydroxy-L-tryptophan, 2-(methylamino)-1H-benzo[de]isoquinoline-1,3(2H)-dione, 5-hydroxy-N-formylkynurenine, DL-tryptophan, phenylalanine, and N-lauroylglycine.

DETAILED DESCRIPTION

Figure 1:
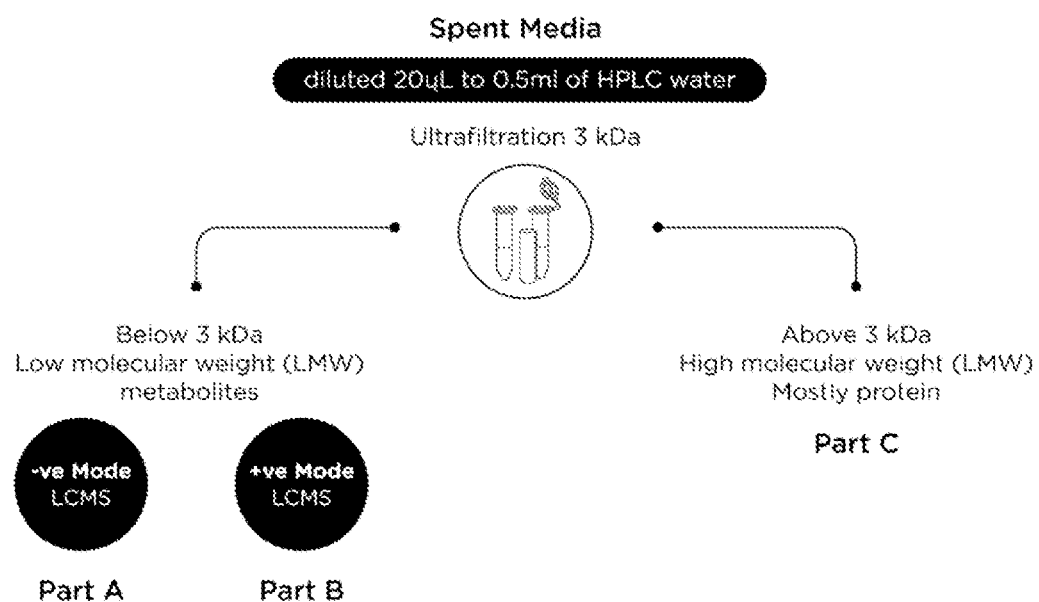
FIG. 1 shows a schematic of protein separation from conditioned media.
Figure 2:
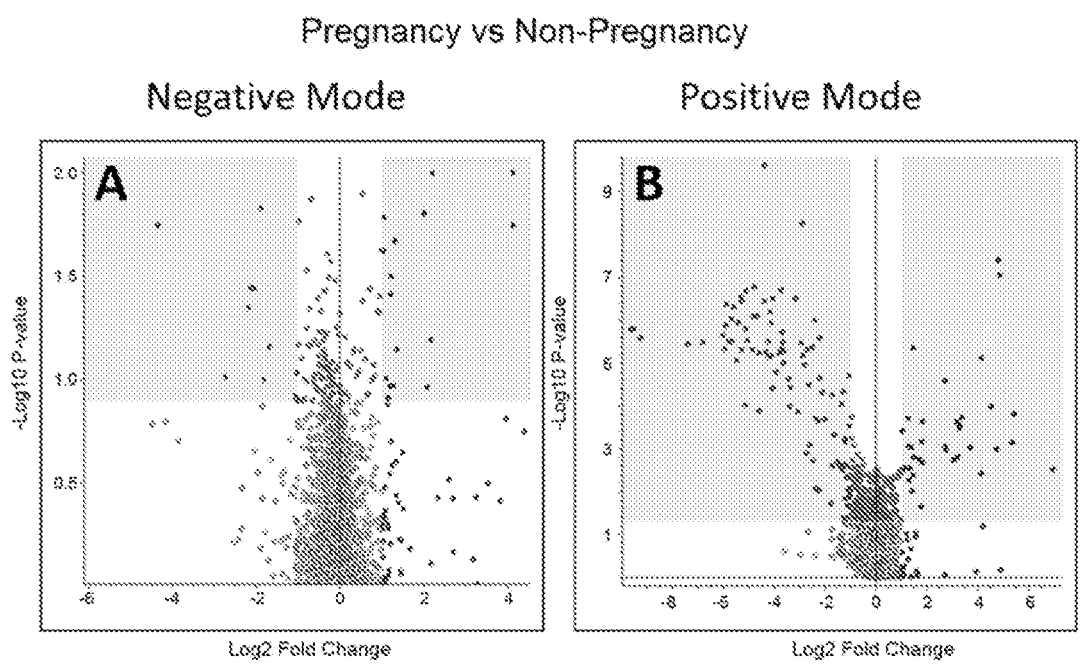
FIG. 2 shows a volcano plot of metabolite abundances detected with negative mode or positive mode mass spectrometry.

Disclosed herein is a method for predicting the implantation success of an embryo during the IVF process. Using a method of the disclosure, one can assess the probability of an embryo's implantation success based on, for example, the concentration of metabolites present in a sample of conditioned embryo culture media.

In Vitro Fertilization.

IVF is a type of ART that involves the fertilization of a female ovum outside of the body. Prior to IVF an ovum must be retrieved from a female subject. Non-limiting examples of female subjects include a human, non-human primate, dog, cow, horse, pig, sheep, goat, cat, buffalo, guinea pig, hamster, rabbit, rat, and mouse. Prior to ovum retrieval, a female's ovaries can be stimulated via the administration of one or more hormones or agents including, for example, inhibin, an inhibin and activin mixture, clomiphene citrate, human menopausal gonadotropins such as follicle stimulating hormone (FSH), and a mixture of FSH and luteinizing hormone (LH), and/or human chorionic gonadotropins.

The retrieval of oocytes can occur through various methods including, for example, transvaginal, ultrasound-guided follicular aspiration, perurethral/transvesical ultrasonographic puncture, or through laparoscopic methods. In some embodiments, immature oocytes can be retrieved and allowed to mature in vitro. In some embodiments, oocytes can be developed from ovarian stem cells, mesenchymal stem cells, or ovarian tissue.

Following retrieval, oocytes are washed and placed in a receptacle such as a dish. After about 2 to 6 hours, eggs are fertilized with sperm via direct injection of sperm into each ovum (intracytoplasmic sperm injection), or by mixing of sperm and oocytes in a dish under conditions that facilitate fertilization. The fertilized oocytes (now embryos) are then cultured in vitro in media for a period of a time, such as 2 to 6 days. Embryo culture conditions can include a temperature approximating that found in vivo (37° C.), sub-ambient concentration of oxygen (usually 5%) and elevated concentrations of carbon dioxide (5-6%). Embryos can be cryopreserved at any time after fertilization occurs.

After the culture period, the embryo transfer process can occur. To facilitate embryo transfer, a speculum can be inserted into the vagina of a subject to open the vaginal walls. A catheter is then passed through the cervix and into the uterine cavity. The optimal placement of the catheter within the uterus is about 1-2 cm from the uterine fundus, and in some instances, catheter placement is guided with ultrasound. Following catheter placement, one or more embryos are passed through the catheter and into the uterus where implantation can occur. Implantation of the embryo into the uterine wall results in pregnancy.

The implantation rate of an embryo following transfer to the uterus is about 30-40% in women under 35 years of age. To improve the efficiency of IVF, clinicians can transfer multiple embryos at once. While transferring multiple embryos at once improves the chances of at least one embryo implanting and thus a successful pregnancy, multiple gestations (i.e., twins, triplets, etc.) can occur. Multiple gestation pregnancies can lead to increased hospital costs, increased rearing burden, and developmental issues. A method disclosed herein can assess the probability of an embryo's implantation success during the embryo culture stage. Knowing the probability of success prior to implantation improves implantation rates and reduces the need for multiple embryo transfers.

Predicting Embryo Implantation Success.

A method of the disclosure can assess the probability of an embryo's implantation success by measuring, for example, the amount of one or more metabolites present in conditioned embryo culture media. Conditioned embryo culture media is culture media that has previously been exposed to an embryo, while fresh culture media is culture media that has not been exposed to an embryo. The presence of metabolites in conditioned embryo culture media can be due to the secretion of the metabolites by the embryo. In some instances, embryos consume or modify metabolites present in fresh embryo culture media causing a change in the amount of the metabolites present in the conditioned embryo culture media. The amount of a specific metabolite present in conditioned embryo culture media can correlate with the probability of implantation success of the cultured embryo. When the amount of a metabolite present in conditioned culture media correlates with a high probability of implantation success, that metabolite suitable as a pregnancy biomarker. When the amount of a metabolite present in conditioned culture media correlates with a low probability of implantation success, the metabolite is suitable as a non-pregnancy biomarker. In some embodiments, a method of the disclosure can predict implantation success of an embryo by comparing the amount of pregnancy vs. non-pregnancy biomarkers present in conditioned culture media.

Discovery of Pregnancy and Non-Pregnancy Biomarkers.

The probing of pregnancy and non-pregnancy biomarkers can be facilitated by, for example, mass spectrometry (MS)-based approaches. MS is an analytical technique that can detect, identify, and quantify molecules, such as metabolites, based on their mass-to-charge (m/z) ratio. The first step in the mass spectrometry process is ionization. Ionization can occur through several different methods. For gaseous or vapor samples, electron ionization or chemical ionization can be used. For solid or liquid biological samples, electrospray ionization (ESI) and matrix-assisted laser desorption/ionization can be used. Other examples of ionization include fast atom bombardment atmospheric-pressure chemical ionization, inductively coupled plasma ionization, photoionization, glow discharge ionization, filed desorption ionization, thermospray ionization, spark ionization, atmospheric pressure chemical ionization, atmospheric pressure photoionization, thermal ionization, and desorption/ionization on silicon. Ionization techniques can be performed that encourage the formation of positive ions (positive mode) or negative ions (negative mode).

Following the ionization of samples, the produced ions are separated according to their m/z ratios. The separation of ions can be performed using several different mass analyzers including, for example, time-of-flight (TOF) analyzers, quadrupole mass analyzers, three-dimensional quadrupole ion traps, cylindrical ion traps, Orbitrap mass analyzers, and Fourier transform ion cyclotron resonance mass analyzers. TOF analyzers use an electric field to accelerate ions through a constant potential and determine the mass of an ion based on the time needed for an ion to reach the detector. In quadrupole mass analyzers, 4 parallel rods create a radio frequency (RF) quadrupole field. Oscillating electric fields are then used to stabilize or destabilize selectively the paths of ions through the RF quadrupole field. At a given time interval, only ions in a certain m/z range pass through the system. Thus, ions are separated.

Three-dimensional quadrupole ion traps function based on the same principles of a quadrupole mass analyzer. However, ions are trapped in a mainly RF-field in a space defined by a ring electrode, and are then sequentially ejected. The ejection of ions is based on the m/z ratio of ions, allowing for separation. Cylindrical ion traps are derivative of quadrupole ion traps, with the difference being that the electrodes are formed from flat rings and are not hyperbolically shaped. Linear ion quadrupole ion traps are similar to quadrupole ion traps, but utilize a two dimensional quadrupole field.

Orbitrap mass analyzers electrostatically trap ions in an orbit around a central, spindle shaped electrode. The electrode traps into oscillation along the electrode's long axis while also orbiting around the electrode. Ion oscillation generates an image current dependent on ion m/z ratio, and can be converted to a mass spectrum by Fourier transformation. Fourier transform ion cyclotron resonance mass analyzers detect the image current produced by ions cyclotroning in the presence of a magnetic field. Ions are injected into a static electric/magnetic ion trap (Penning trap) and effectively form part of a circuit. As ions pass near detectors, electrical signals are measured over time, producing a periodic signal with a frequency dependent on the ion's m/z ratio. Using Fourier transformation, the periodic signal can be deconvolved to obtain a mass spectrum.

Mass spectrometry can be performed in multiple rounds in a process known as tandem mass spectrometry (MS/MS). Rounds of mass spectrometry can be separated by molecule fragmentation. Thus, MS/MS can have the steps of ionization, m/z separation to produce an MS' precursor ion, fragmentation of the MS' precursor ion, and m/z separation to produce an $MS^2$ product ion, followed by detection. Methods for fragmentation include, for example, collision-induced dissociation (CID), higher-energy collisional dissociation (HCD), electron capture dissociation (ECD), electron transfer dissociation (ETD), infrared multiphoton dissociation (IRMPD), blackbody infrared radiative dissociation (BIRD), electron-detachment dissociation (EDD) and surface-induced dissociation (SID).

The ability of MS-based approaches to identify molecules in a complex mixture can be enhanced by combining MS-based approaches with separation techniques. Combining MS approaches with separation techniques allows for the analysis of pre-separated samples. Separation techniques that can be combined with MS-based approaches include, for example, high performance liquid chromatography (HPLC), gas chromatography (GC), ultra-performance liquid chromatography (UPLC), ion chromatography (IC), and capillary electrophoresis (CE).

Non-limiting examples of MS-based approaches that can be used to identify pregnancy or non-pregnancy biomarkers in conditioned media include Fourier transform ion cyclotron resonance-mass spectrometry (FTICR-MS), Fusion Orbitrap MS, UPLC-coupled Fusion Orbitrap MS, collision-induced-dissociation-tandem MS (CID-MS/MS), higher-energy collisional dissociation-coupled tandem MS (HCD-MS/MS), infrared multiphoton dissociation—tandem MS (IRMPD-MS/MS), liquid chromatography triple quadrupole tandem mass spectrometry (LC-QqQ-MS), GC-MS, LC-MS, IC-MS, and capillary electrophoresis-MS (CE-MS).

Completion of MS or MS/MS techniques produces a plot of intensity vs. m/z ratio known as a mass spectrum. The mass spectrum represents the distribution of ions in a sample by m/z ratio. From this distribution the identity of a molecule can be determined. Combining separation techniques with MS approaches allows for separation, analysis, and identification of individual molecules such as pregnancy or non-pregnancy biomarkers from a complex mixture such as conditioned media. In some instances, techniques disclosed herein can identify molecules such as pregnancy or non-pregnancy biomarkers by, for example, molecular weight, chromatographic retention time, mass spectra fragmentation pattern, chemical name, chemical formula, chemical structure, or any combination thereof. Moreover, because the intensity of a molecule's mass spectrum correlates with abundance, MS-based approaches can be used to quantify the amount of a molecule such as a pregnancy or non-pregnancy biomarker present in a sample such as conditioned media.

A metabolite can be identified as a pregnancy of non-pregnancy biomarker if the amount of the metabolite present in embryo conditioned media correlates with a specific pregnancy outcome, such as a successful or non-successful embryo implantation. To determine whether the amount of a metabolite correlates with a pregnancy outcome, statistical methods such as volcano plots can be employed. To produce a volcano plot, the fold change of a measurement of interest between two samples is determined. In some embodiments, the measurement of interest is the abundance of a metabolite in the samples. In some embodiments, the two samples are conditioned media from an embryo resulting in a successful pregnancy and conditioned media from an embryo that did not result in a successful pregnancy. A p-value is also calculated to assess the statistical significance of the change of the measurement seen between the two sample groups. The −log 10(p-value) is then plotted vs. the −log 2(fold change). By setting cut-off values for −log 10(p-value) and −log 2(fold change), biomarkers that correlate with pregnancy or non-pregnancy can be identified.

Biomarker Based Assessments.

A pregnancy or non-pregnancy biomarker can be present in conditioned culture media at any time after fertilization has occurred and embryo culture has begun. In some embodiments, a pregnancy or non-pregnancy biomarker is present in media after about 0.05 days to about 8 days of embryo culture. In some embodiments a pregnancy or non-pregnancy biomarker is present in media after: about 0.05 days to about 0.1 days, about 0.05 days to about 0.2 days, about 0.05 days to about 0.5 days, about 0.05 days to about 1 day, about 0.05 days to about 2 days, about 0.05 days to about 3 days, about 0.05 days to about 4 days, about 0.05 days to about 5 days, about 0.05 days to about 6 days, about 0.05 days to about 7 days, about 0.05 days to about 8 days, about 0.1 days to about 0.2 days, about 0.1 days to about 0.5 days, about 0.1 days to about 1 day, about 0.1 days to about 2 days, about 0.1 days to about 3 days, about 0.1 days to about 4 days, about 0.1 days to about 5 days, about 0.1 days to about 6 days, about 0.1 days to about 7 days, about 0.1 days to about 8 days, about 0.2 days to about 0.5 days, about 0.2 days to about 1 day, about 0.2 days to about 2 days, about 0.2 days to about 3 days, about 0.2 days to about 4 days, about 0.2 days to about 5 days, about 0.2 days to about 6 days, about 0.2 days to about 7 days, about 0.2 days to about 8 days, about 0.5 days to about 1 day, about 0.5 days to about 2 days, about 0.5 days to about 3 days, about 0.5 days to about 4 days, about 0.5 days to about 5 days, about 0.5 days to about 6 days, about 0.5 days to about 7 days, about 0.5 days to about 8 days, about 1 day to about 2 days, about 1 day to about 3 days, about 1 day to about 4 days, about 1 day to about 5 days, about 1 day to about 6 days, about 1 day to about 7 days, about 1 day to about 8 days, about 2 days to about 3 days, about 2 days to about 4 days, about 2 days to about 5 days, about 2 days to about 6 days, about 2 days to about 7 days, about 2 days to about 8 days, about 3 days to about 4 days, about 3 days to about 5 days, about 3 days to about 6 days, about 3 days to about 7 days, about 3 days to about 8 days, about 4 days to about 5 days, about 4 days to about 6 days, about 4 days to about 7 days, about 4 days to about 8 days, about 5 days to about 6 days, about 5 days to about 7 days, about 5 days to about 8 days, about 6 days to about 7 days, about 6 days to about 8 days, or about 7 days to about 8 days of embryo culture. In some embodiments a pregnancy or non-pregnancy biomarker is present in media after: about 0.05 days, about 0.1 days, about 0.2 days, about 0.5 days, about 1 day, about 2 days, about 3 days, about 4 days, about 5 days, about 6 days, about 7 days, or about 8 days of embryo culture. In some embodiments a pregnancy or non-pregnancy biomarker is present in media after at least: about 0.05 days, about 0.1 days, about 0.2 days, about 0.5 days, about 1 day, about 2 days, about 3 days, about 4 days, about 5 days, about 6 days, or about 7 days of embryo culture. In some embodiments a pregnancy or non-pregnancy biomarker is present in media after at most: about 0.1 days, about 0.2 days, about 0.5 days, about 1 day, about 2 days, about 3 days, about 4 days, about 5 days, about 6 days, about 7 days, or about 8 days of embryo culture.

Conditioned media can be collected at any time after culture has begun to determine the presence or amount of a pregnancy or non-pregnancy biomarker in conditioned media. In some embodiments, media is collected after: about 0.05 days to about 8 days of embryo culture. In some embodiments, media is collected after: about 0.05 days to about 0.1 days, about 0.05 days to about 0.2 days, about 0.05 days to about 0.5 days, about 0.05 days to about 1 day, about 0.05 days to about 2 days, about 0.05 days to about 3 days, about 0.05 days to about 4 days, about 0.05 days to about 5 days, about 0.05 days to about 6 days, about 0.05 days to about 7 days, about 0.05 days to about 8 days, about 0.1 days to about 0.2 days, about 0.1 days to about 0.5 days, about 0.1 days to about 1 day, about 0.1 days to about 2 days, about 0.1 days to about 3 days, about 0.1 days to about 4 days, about 0.1 days to about 5 days, about 0.1 days to about 6 days, about 0.1 days to about 7 days, about 0.1 days to about 8 days, about 0.2 days to about 0.5 days, about 0.2 days to about 1 day, about 0.2 days to about 2 days, about 0.2 days to about 3 days, about 0.2 days to about 4 days, about 0.2 days to about 5 days, about 0.2 days to about 6 days, about 0.2 days to about 7 days, about 0.2 days to about 8 days, about 0.5 days to about 1 day, about 0.5 days to about 2 days, about 0.5 days to about 3 days, about 0.5 days to about 4 days, about 0.5 days to about 5 days, about 0.5 days to about 6 days, about 0.5 days to about 7 days, about 0.5 days to about 8 days, about 1 day to about 2 days, about 1 day to about 3 days, about 1 day to about 4 days, about 1 day to about 5 days, about 1 day to about 6 days, about 1 day to about 7 days, about 1 day to about 8 days, about 2 days to about 3 days, about 2 days to about 4 days, about 2 days to about 5 days, about 2 days to about 6 days, about 2 days to about 7 days, about 2 days to about 8 days, about 3 days to about 4 days, about 3 days to about 5 days, about 3 days to about 6 days, about 3 days to about 7 days, about 3 days to about 8 days, about 4 days to about 5 days, about 4 days to about 6 days, about 4 days to about 7 days, about 4 days to about 8 days, about 5 days to about 6 days, about 5 days to about 7 days, about 5 days to about 8 days, about 6 days to about 7 days, about 6 days to about 8 days, or about 7 days to about 8 days of embryo culture. In some embodiments conditioned media is collected after at least: about 0.05 days, about 0.1 days, about 0.2 days, about 0.5 days, about 1 day, about 2 days, about 3 days, about 4 days, about 5 days, about 6 days, or about 7 days of embryo culture. In some embodiments conditioned media is collected: at most about 0.1 days, about 0.2 days, about 0.5 days, about 1 day, about 2 days, about 3 days, about 4 days, about 5 days, about 6 days, about 7 days, or about 8 days of embryo culture.

The probability of an embryo's implantation success can be assessed based on the amount of one or more biomarkers present in conditioned media. A biomarker can be a pregnancy or non-pregnancy biomarker. In some embodiments an embryo's implantation success is based on the amount of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000 pregnancy or non-pregnancy biomarkers, or any combination thereof.

In some embodiments, an embryo's probability of implantation success can be assessed based on an amount of about 1 biomarker to about 1,000 biomarkers. In some embodiments, an embryo's implantation success can be assessed based on an amount of about 1 biomarker to about 10 biomarkers, about 1 biomarker to about 50 biomarkers, about 1 biomarker to about 100 biomarkers, about 1 biomarker to about 200 biomarkers, about 1 biomarker to about 500 biomarkers, about 1 biomarker to about 750 biomarkers, about 1 biomarker to about 1,000 biomarkers, about 10 biomarkers to about 50 biomarkers, about 10 biomarkers to about 100 biomarkers, about 10 biomarkers to about 200 biomarkers, about 10 biomarkers to about 500 biomarkers, about 10 biomarkers to about 750 biomarkers, about 10 biomarkers to about 1,000 biomarkers, about 50 biomarkers to about 100 biomarkers, about 50 biomarkers to about 200 biomarkers, about 50 biomarkers to about 500 biomarkers, about 50 biomarkers to about 750 biomarkers, about 50 biomarkers to about 1,000 biomarkers, about 100 biomarkers to about 200 biomarkers, about 100 biomarkers to about 500 biomarkers, about 100 biomarkers to about 750 biomarkers, about 100 biomarkers to about 1,000 biomarkers, about 200 biomarkers to about 500 biomarkers, about 200 biomarkers to about 750 biomarkers, about 200 biomarkers to about 1,000 biomarkers, about 500 biomarkers to about 750 biomarkers, about 500 biomarkers to about 1,000 biomarkers, about 750 biomarkers to about 1,000 biomarkers, about 12 biomarkers to about 35 biomarkers, about 12 biomarkers to about 36 biomarkers, about 20 biomarkers to about 82 biomarkers, or about 20 biomarkers to about 90 biomarkers. In some embodiments, an embryo's implantation success can be assessed based on an amount of about 1 biomarker, about 10 biomarkers, about 50 biomarkers, about 100 biomarkers, about 200 biomarkers, about 500 biomarkers, about 750 biomarkers, or about 1,000 biomarkers. In some embodiments an embryo's implantation success can be assessed based on an amount of at least about 1 biomarker, about 10 biomarkers, about 50 biomarkers, about 100 biomarkers, about 200 biomarkers, about 500 biomarkers, or about 750 biomarkers. In some embodiments, an embryo's implantation success can be assessed based on an amount of at most about 10 biomarkers, about 50 biomarkers, about 100 biomarkers, about 200 biomarkers, about 500 biomarkers, about 750 biomarkers, or about 1,000 biomarkers. A biomarker can be a pregnancy or non-pregnancy biomarker. In some embodiments, an embryo's probability of implantation success can be assessed based on a combination of amounts of pregnancy and non-pregnancy biomarkers.

In some embodiments, an embryo's probability of implantation success can be assessed based on the amount of one or more pregnancy biomarkers present in conditioned media. In some embodiments, an embryo's probability of implantation success can be assessed based on the amount of one or more non-pregnancy biomarkers in conditioned media. In some embodiments, an embryo's probability of implantation success can be assessed based on a comparison of the amount of one or more pregnancy biomarkers to the amount of one or more non-pregnancy biomarkers present in conditioned media. In some embodiments, assessment of an embryo's probability of implantation success is based on a definite amount of one or more pregnancy or non-pregnancy biomarkers. In some embodiments, assessment of an embryo's probability of implantation success is based on a relative amount of one or more pregnancy or non-pregnancy biomarkers.

Accuracy of Predictions.

A method of the disclosure can make a prediction on the implantation success of an embryo. The prediction can be made based on, for example, an assessment of the probability of implantation success of the embryo. The probability of an embryo's implantation success can be based on the presence of pregnancy or non-pregnancy biomarkers in embryo conditioned media. In some embodiments, when predicting whether an embryo will successfully implant, a method of the disclosure has an accuracy of about 70% to about 99.9%. In some embodiments, when predicting whether an embryo will successfully implant, a method of the disclosure has an accuracy of about 70% to about 75%, about 70% to about 80%, about 70% to about 85%, about 70% to about 90%, about 70% to about 95%, about 70% to about 96%, about 70% to about 97%, about 70% to about 98%, about 70% to about 99%, about 70% to about 99.9%, about 75% to about 80%, about 75% to about 85%, about 75% to about 90%, about 75% to about 95%, about 75% to about 96%, about 75% to about 97%, about 75% to about 98%, about 75% to about 99%, about 75% to about 99.9%, about 80% to about 85%, about 80% to about 90%, about 80% to about 95%, about 80% to about 96%, about 80% to about 97%, about 80% to about 98%, about 80% to about 99%, about 80% to about 99.9%, about 85% to about 90%, about 85% to about 95%, about 85% to about 96%, about 85% to about 97%, about 85% to about 98%, about 85% to about 99%, about 85% to about 99.9%, about 90% to about 95%, about 90% to about 96%, about 90% to about 97%, about 90% to about 98%, about 90% to about 99%, about 90% to about 99.9%, about 95% to about 96%, about 95% to about 97%, about 95% to about 98%, about 95% to about 99%, about 95% to about 99.9%, about 96% to about 97%, about 96% to about 98%, about 96% to about 99%, about 96% to about 99.9%, about 97% to about 98%, about 97% to about 99%, about 97% to about 99.9%, about 98% to about 99%, about 98% to about 99.9%, or about 99% to about 99.9%. In some embodiments, when predicting whether an embryo will successfully implant, a method of the disclosure has an accuracy of about 70%, about 75%, about 80%, about 85%, about 90%, about 95%, about 96%, about 97%, about 98%, about 99%, or about 99.9%. In some embodiments, when predicting whether an embryo will successfully implant, a method of the disclosure has accuracy of at least about 70%, at least about 75%, at least about 80%, at least about 85%, at least about 90%, at least about 95%, at least about 96%, at least about 97%, at least about 98%, at least or about 99%.

Detection Methods.

The amount of a metabolite such as a pregnancy or non-pregnancy biomarker present in conditioned culture media can be measured with various detection methods. Non-limiting examples of detection methods that can be used to identify or measure amounts of metabolites include colorimetric assays; optical assays such as fluorescence assays, ultraviolet light (UV) absorbance assays, luminescence assays, and phosphorescence assays; ligand binding assays such as dual polarization interferometry, enzyme-linked immunoabsorbent assays (ELISA), magnetic immunoassays, and radioimmunoassays; spectroscopic assays such as nuclear magnetic resonance (NMR) spectroscopy, Fourier transform infrared (FTIR) spectroscopy, and near infrared spectroscopy (NIR); electrophoresis based assays; nanoparticle-based assays; chromatographic assays such as high performance liquid chromatography (HPLC), gas chromatography (GC), ultra-performance liquid chromatography (UPLC), ion chromatography (IC), capillary electrophoresis (CE) and supercritical fluid chromatography; and MS-based approaches such as FTICR-MS, Orbitrap MS, time of flight-MS (TOF-MS), single quad mass spectroscopy (Q-MS), ion trap mass spectroscopy (IT-MS); tandem based mass spectroscopy such as collision-induced-dissociation-tandem MS (CID-MS/MS), higher-energy collisional dissociation-coupled tandem MS (HCD-MS/MS), infrared multiphoton dissociation-tandem MS (IRMPD-MS/MS); coupled chromatography with mass spectroscopy techniques such as liquid chromatography triple quadrupole tandem mass spectrometry (LC-QqQ-MS), GC-MS, LC-MS, IC-MS, and capillary electrophoresis-MS (CE-MS). In some embodiments, combination of the aforementioned detection methods can be used to measure the amount of one or more metabolites (e.g., pregnancy or non-pregnancy biomarkers) in a sample of conditioned culture media.

The metabolites that are produced, consumed, or modified by an embryo can vary depending on the type of media in which the embryo is cultured. Thus, the classification of a metabolite as a pregnancy or non-pregnancy biomarker can differ depending on an embryo's culture media. Non-limiting examples of media that can be used for embryo culture include SAGE™ In-Vitro Maturation Media (IVM), Vitrolife G-TL™ media, Origio SAGE 1-Step™ media, Cook Medical Sydney IVF Cleavage Medium, Irvine Continuous Single Culture® Complete product (CSCM-C) with Human Serum Albumin, LifeGlobal® Global® Total®, and FertiPro FertiCult™ IVF medium.

Pregnancy Biomarkers.

Non-limiting examples of pregnancy biomarkers that can be utilized in a method of the disclosure are shown below in TABLE 1A and TABLE 1B. TABLE 1A shows details on biomarker chemical formulas, molecular weight, retention time, and MS fragmentation list. TABLE 1B shows corresponding chemical structures of compounds listed in TABLE 1A.

TABLE 1A

| NO. | Name | Formula | Molecular Weight | RT [min] | Fragmentation list |
|---|---|---|---|---|---|
| 1 | Caprolactam | $C_6H_{11}NO$ | 113.08393 | 6.483 | 52.9, 54.1, 54.9, 56.8, 60.9, 67.0, 67.9, 68.9, 70.0, 71.0, 72.0, 72.9, 73.6, 76.9, 79.0, 79.9, 80.9, 83.9, 85.1, 85.9, 90.9, 95.0, 96.1, 97.0, 98.0, 105.0, 114.0 |
| 2 | N-Cyclohexylformamide | $C_7H_{13}NO$ | 127.09952 | 7.616 | 52.8, 54.0, 54.8, 55.7, 56.8, 57.9, 67.0, 67.8, 69.0, 69.8, 70.9, 71.9, 74.2, 79.7, 81.9, 83.0, 84.1, 86.0, 91.4, 98.1, 100.0, 101.8, 109.8, 111.4, 117.7, 128.0 |
| 3 | — | $C_9H_6O$ | 130.04175 | 3.39 | 54.8, 56.8, 62.8, 71.9, 73.1, 74.9, 76.9, 94.9, 103.0, 103.9, 105.0, 107.8, 131.0 |
| 4 | — | $C_9H_6O$ | 130.0418 | 3.114 | 50.9, 56.8, 58.8, 61.1, 63.0, 66.9, 70.0, 71.8, 73.0, 76.9, 78.9, 85.1, 90.0, 91.0, 94.9, 95.6, 100.8, 102.1, 102.9, 103.7, 104.9, 108.0, 118.1, 126.1, 130.8 |
| 5 | Threo-3-hydroxy-2-methylbutyric acid | $C_6H_{12}O_3$ | 132.07852 | 6.487 | 50.8, 52.8, 56.8, 66.1, 69.2, 72.9, 76.7, 86.8, 87.9, |

TABLE 1A-continued

| NO. | Name | Formula | Molecular Weight | RT [min] | Fragmentation list |
|---|---|---|---|---|---|
| 6 | — | $C_4H_{11}O_3P$ | 138.04421 | 6.238 | 88.8, 95.0, 131.3, 133.1 56.7, 58.7, 59.7, 62.9, 64.8, 73.0, 77.0, 79.8, 81.1, 81.9, 93.1, 95.1, 97.8, 98.8, 100.9, 112.2, 116.0, 116.8, 118.8, 120.9, 138.8 |
| 7 | Sulfoacetic acid | $C_2H_4O_5S$ | 139.94387 | 0.382 | 52.2, 54.7, 56.7, 58.9, 67.1, 67.8, 80.9, 81.9, 85.0, 85.8, 88.8, 93.1, 94.9, 98.9, 100.0, 114.8, 115.8, 116.9, 117.9, 125.8, 130.8, 135.8, 140.9 |
| 8 | — | $C_6H_{14}O_4$ | 150.08909 | 6.383 | 57.0, 57.6, 66.0, 68.8, 72.9, 77.9, 78.9, 88.8, 103.1, 132.8 |
| 9 | Phenylalanine | $C_9H_{11}NO_2$ | 165.07875 | 3.392 | 50.9, 53.9, 56.8, 64.7, 66.9, 67.9, 73.9, 77.0, 77.8, 79.0, 80.0, 83.8, 85.6, 88.1, 91.1, 92.0, 93.1, 94.0, 95.0, 95.9, 99.1, 102.2, 103.0, 104.1, 105.0, 105.8, 107.0, 107.8, 111.9, 114.1, 117.4, 118.0, 120.0, 120.8, 121.7, 123.1, 129.0, 131.0, 135.2, 139.7, 149.0, 166.0 |
| 10 | — | — | 174.55215 | 3.813 | 54.7, 55.8, 56.9, 66.0, 66.8, 69.0, 69.9, 84.9, 86.9, 95.3, 96.2, 100.1, 108.0, 117.8, 123.9, 127.8, 130.2, 131.0, 146.9, 174.9 |
| 11 | (2,7-Dimethyloctahydro-1H-cyclopenta[c]pyridin-4-yl)methanol | $C_{11}H_{21}NO$ | 183.16204 | 7.552 | 56.7, 66.8, 70.9, 72.9, 74.9, 81.0, 82.1, 82.9, 87.0, 95.9, 101.8, 104.5, 110.8, 112.9, 114.8, 116.8, 117.9, 123.9, 128.0, 131.9, 132.8, 139.8, 142.1, 144.2, 146.9, 147.9, 161.0, 163.8, 184.2 |
| 12 | — | $C_5H_{10}N_6O_2$ | 186.08652 | 3.134 | 54.6, 56.3, 56.9, 66.9, 67.9, 70.1, 72.8, 79.1, 80.8, 82.9, 88.0, 89.1, 90.8, 95.0, 97.0, 99.0, 103.2, 107.2, 112.9, 113.9, 114.9, 118.6, 119.9, 133.8, 168.8 |
| 13 | Trans-3-indoleacrylic acid | $C_{11}H_9NO_2$ | 187.06307 | 5.766 | 54.8, 56.7, 58.9, 65.1, 67.9, 70.8, 72.9, 73.8, 76.9, 78.1, 87.9, 88.9, 89.9, 91.0, 95.0, |

TABLE 1A-continued

| NO. | Name | Formula | Molecular Weight | RT [min] | Fragmentation list |
|---|---|---|---|---|---|
| | | | | | 99.0, 101.0, 103.0, 103.9, 105.0, 106.0, 109.1, 113.9, 115.0, 116.0, 117.0, 118.0, 119.1, 120.1, 121.1, 127.0, 128.0, 129.0, 130.1, 132.0, 134.0, 134.8, 140.1, 141.3, 142.0, 143.0, 144.0, 145.0, 146.1, 146.8, 150.1, 155.0, 159.9, 164.8, 169.2, 170.0, 172.8, 176.1, 187.9 |
| 14 | DL-Tryptophan | $C_{11}H_{12}N_2O_2$ | 204.08955 | 5.874 | 56.7, 57.8, 70.9, 74.0, 78.9, 91.0, 101.9, 105.1, 113.8, 115.0, 116.0, 117.1, 118.0, 119.0, 126.9, 128.1, 129.1, 129.9, 131.3, 132.0, 133.0, 134.0, 140.4, 142.0, 143.0, 144.0, 145.1, 146.0, 146.9, 154.3, 154.9, 159.0, 159.9, 170.1, 170.7, 187.1, 188.0, 199.3, 205.1 |
| 15 | — | $C_{12}H_{25}NO_2$ | 215.18839 | 2.71 | — |
| 16 | Pantothenic acid | $C_9H_{17}NO_5$ | 219.11024 | 3.812 | 57.0, 59.1, 66.8, 67.9, 68.9, 69.9, 71.8, 72.9, 81.1, 85.0, 90.0, 91.0, 93.8, 95.1, 97.9, 100.0, 100.8, 102.9, 105.0, 112.1, 113.0, 113.9, 115.9, 122.1, 124.1, 134.7, 142.2, 156.1, 159.8, 183.9, 202.0, 220.0 |
| 17 | — | — | 219.13875 | 5.396 | — |
| 18 | — | $C_{10}H_{16}N_2O_2S$ | 228.09711 | 2.618 | 52.9, 54.9, 56.8, 60.8, 63.8, 68.9, 79.0, 80.9, 81.9, 87.1, 90.8, 94.8, 97.0, 98.9, 101.0, 103.1, 105.0, 107.1, 109.2, 110.8, 112.8, 114.6, 116.9, 118.9, 120.9, 121.8, 123.0, 123.9, 124.9, 126.9, 128.9, 130.9, 133.0, 134.0, 134.9, 136.9, 138.2, 138.9, 139.8, 140.8, 142.9, 144.9, 145.6, 146.9, 148.1, 148.9, 150.2, 150.9, 152.9, |

TABLE 1A-continued

| NO. | Name | Formula | Molecular Weight | RT [min] | Fragmentation list |
|---|---|---|---|---|---|
| | | | | | 154.2, 154.9, 156.2, 156.9, 157.8, 158.7, 159.8, 161.0, 166.0, 166.8, 167.6, 168.9, 169.5, 171.8, 172.9, 173.5, 174.7, 177.9, 180.9, 191.0, 193.2, 196.0, 197.1, 199.0, 208.9, 211.2, 229.0 |
| 19 | — | $C_{10}H_{22}O_6$ | 238.14117 | 6.555 | 62.8, 68.9, 73.1, 75.1, 84.8, 87.0, 88.9, 89.6, 90.7, 94.0, 96.9, 102.0, 107.0, 112.7, 117.0, 130.1, 130.9, 133.0, 147.9, 153.1, 156.8, 165.8, 166.7, 178.3, 179.0, 210.2 |
| 20 | — | $C_{10}H_{22}O_6$ | 238.14118 | 6.461 | 54.8, 56.6, 57.2, 73.0, 87.0, 88.9, 102.0, 107.3, 130.9, 133.0, 133.8, 135.0, 147.9, 148.9, 150.9, 152.2, 156.8, 167.0, 188.0 |
| 21 | — | $C_{10}H_{22}O_6$ | 238.14122 | 6.256 | 54.8, 86.9, 89.0, 89.7, 91.5, 107.0, 116.7, 130.8, 133.0, 133.8, 207.8 |
| 22 | — | $C_{10}H_{22}O_6$ | 238.14123 | 5.999 | 58.8, 61.0, 63.0, 82.8, 86.9, 89.0, 89.9, 91.0, 96.0, 107.0, 116.8, 118.1, 119.0, 124.0, 132.1, 133.0, 133.8, 135.0, 135.8, 151.1, 165.7, 167.7, 209.8 |
| 23 | — | $C_8H_{14}N_6O_3$ | 242.11265 | 6.785 | — |
| 24 | — | $C_{11}H_{25}NO_5$ | 251.17303 | 2.62 | 54.9, 59.9, 86.9, 97.2, 104.0, 129.0, 132.1, 134.7, 141.8, 156.1, 163.3, 165.0 |
| 25 | — | $C_4H_5N_2O_5P_3$ | 253.94165 | 0.382 | 54.8, 56.9, 90.8, 107.1, 112.9, 116.7, 118.7, 123.2, 130.9, 132.1, 133.0, 144.9, 148.8, 151.5, 152.8, 159.9, 169.9, 174.7, 176.7, 184.0 |
| 26 | — | $C_{17}H_{18}S$ | 254.1125 | 8.055 | 82.8, 94.8, 149.1, 183.2, 197.1, 255.0 |
| 27 | — | $C_{13}H_{12}N_2O_4$ | 260.07929 | 3.2 | 56.7, 58.7, 76.7, 85.0, 101.0, 109.7, 127.9, 130.0, 130.9, 131.9, 146.1, 148.9, 150.9, 155.1, 155.9, 157.0, 158.0, |

TABLE 1A-continued

| NO. | Name | Formula | Molecular Weight | RT [min] | Fragmentation list |
|---|---|---|---|---|---|
| | | | | | 169.3, 173.0, 174.1, 176.2, 183.1, 202.1, 205.1 |
| 28 | Diaveridine | $C_{13}H_{16}N_4O_2$ | 260.12319 | 6.219 | 112.9, 128.9, 130.9, 140.8, 156.3, 158.1, 160.8, 168.7, 174.0, 261.1 |
| 29 | 5-Benzyl-3,6-dioxo-2-piperazinyl)acetic acid | $C_{13}H_{14}N_2O_4$ | 262.09492 | 3.36 | 56.9, 63.5, 69.4, 71.0, 85.1, 91.1, 92.8, 93.9, 101.9, 107.9, 117.1, 130.0, 132.0, 133.1, 135.1, 142.1, 145.8, 147.1, 149.2, 155.8, 156.9, 157.9, 159.0, 160.0, 165.0, 167.8, 170.8, 171.9, 175.1, 175.9, 181.5, 184.9, 185.9, 203.0, 204.7, 215.1, 220.7, 263.0 |
| 30 | — | $C_9H_{14}N_6O_4$ | 270.10738 | 8.347 | 107.5, 133.0, 136.9, 142.9, 143.9, 148.1, 148.8, 150.0, 153.1, 164.0, 182.2, 225.1, 271.2 |
| 31 | — | — | 283.19887 | 6.462 | 70.9, 73.0, 86.9, 88.9, 89.8, 91.1, 106.9, 115.1, 130.6, 133.0, 133.8, 151.0, 156.7, 159.1, 163.8, 177.1, 195.2, 284.1 |
| 32 | — | — | 283.19888 | 6.552 | 72.9, 86.9, 88.9, 89.8, 106.1, 107.0, 121.2, 131.3, 133.0, 133.7, 148.9, 150.9, 156.3, 163.8, 177.1, 195.1, 238.8 |
| 33 | — | — | 283.19901 | 6.245 | 52.6, 87.0, 89.0, 90.0, 91.1, 133.0, 151.0, 177.0, 195.1, 239.1, 284.0 |
| 34 | — | $C_9H_{16}N_6O_5$ | 288.11798 | 2.481 | 54.9, 57.0, 88.8, 95.0, 98.7, 115.1, 123.1, 130.8, 133.1, 144.9, 154.9, 156.2, 158.8, 160.9, 162.9, 167.8, 171.0, 172.9, 179.2, 187.6, 197.0, 271.2, 289.1 |
| 35 | — | $C_{14}H_{22}N_2OS$ | 288.11805 | 3.294 | 56.9, 67.0, 69.0, 71.0, 129.0, 131.7, 149.1, 152.9, 154.8, 156.6, 166.6, 168.9, 171.0, 172.7, 184.8, 288.9 |
| 36 | Dasytrichone | $C_{18}H_{16}O_4$ | 296.10462 | 3.391 | 57.0, 65.0, 66.8, 72.7, 73.9, 75.0, 76.9, 79.0, 79.9, |

TABLE 1A-continued

| NO. | Name | Formula | Molecular Weight | RT [min] | Fragmentation list |
|---|---|---|---|---|---|
| | | | | | 91.1, 93.1, 95.0, 95.9, 103.1, 104.9, 106.0, 107.0, 107.9, 121.0, 122.0, 130.0, 131.0, 149.1, 151.0 |
| 37 | — | $C_4H_3N_1S_2Cl_2$ | 198.9091 | 0.465 | 74.1, 92.0, 93.0, 95.9, 98.0, 107.8, 109.0, 113.9, 115.7, 116.8, 121.9, 126.1, 135.8, 140.9, 141.8, 160.7, 161.4, 162.8, 180.0, 197.7 |
| 38 | — | $C_9H_8S_3$ | 211.9788 | 1.979 | 58.7, 75.1, 89.0, 91.0, 96.9, 115.1, 122.0, 129.1, 135.0, 136.9, 142.8, 153.0, 167.0 |
| 39 | — | $C_4H_2N_2O_5S_2$ | 237.9354 | 0.465 | — |
| 40 | — | $C_{10}H_{23}N_4O_3P_1$ | 278.1511 | 21.081 | — |
| 41 | — | $C_{16}H_{30}O_4$ | 286.2141 | 20.625 | 58.9, 105.0, 109.2, 138.9, 146.8, 154.9, 170.9, 179.4, 184.9, 212.9, 223.2, 235.2, 285.4 |
| 42 | — | $C_6H_5N_6O_4S_1P_1$ | 287.9829 | 17.412 | 97.1, 102.0, 109.0, 113.1, 130.8, 136.9, 141.0, 143.0, 145.8, 154.9, 156.9, 160.9, 167.7, 178.9, 184.3, 190.8, 199.1, 201.0, 206.9, 215.0, 246.8, 255.8, 265.4, 286.5 |
| 43 | — | $C_3H_3N_2O_5S_3P_1Cl_1$ | 308.8630 | 21.566 | — |
| 44 | — | $C_2H_3O_4S_2P_3Cl_2$ | 317.8076 | 20.962 | 92.9, 112.9, 126.9, 135.8, 136.8, 140.6, 156.5, 168.7, 170.6, 180.7, 192.7, 229.2 |
| 45 | — | $C_{12}H_{23}N_4O_4P_1$ | 318.1457 | 20.87 | 59.1, 92.9, 98.9, 99.7, 101.0, 113.0, 114.9, 116.6, 125.0, 126.9, 128.2, 128.9, 137.0, 141.0, 142.0, 142.9, 144.5, 153.2, 154.0, 155.0, 157.0, 158.0, 161.9, 171.2, 171.9, 172.9, 188.1, 189.0, 203.0, 213.1, 214.5, 215.1, 229.1, 256.8, 299.2, 315.1, 317.3 |
| 46 | — | $C_9H_{13}N_2O_7S_1P_1$ | 324.0181 | 6.025 | — |
| 47 | — | $C_3H_3N_2O_4S_3P_1Cl_2$ | 327.8370 | 24.329 | 92.8, 97.3, 103.0, 130.6, 136.9, 146.9, 157.0, 185.5, 190.5, 243.2, 266.7 |
| 48 | — | $C_8H_{13}N_2O_7S_2P_1$ | 343.9902 | 18.101 | — |
| 49 | — | $C_9H_{14}O_{10}P_2$ | 344.0062 | 19.623 | — |
| 50 | — | $C_{23}H_{47}N_1O_5$ | 417.3454 | 22.654 | — |

TABLE 1A-continued

| NO. | Name | Formula | Molecular Weight | RT [min] | Fragmentation list |
|---|---|---|---|---|---|
| 51 | — | $C_{18}H_{11}N_2O_8S_1P_1$ | 445.9974 | 20.088 | — |
| 52 | — | $C_7H_3O_{13}S_3P_3$ | 483.7949 | 20.923 | — |

TABLE 1B

| NO. | Structure | Name | Formula |
|---|---|---|---|
| 1 | 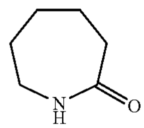 | Caprolactam | $C_6H_{11}NO$ |
| 2 | 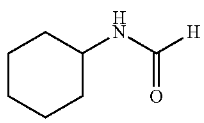 | N-Cyclohexylformamide | $C_7H_{13}NO$ |
| 5 | 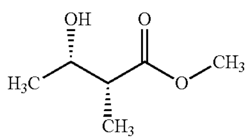 | Threo-3-hydroxy-2-methylbutyric acid | $C_6H_{12}O_3$ |
| 7 | 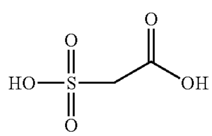 | Sulfoacetic acid | $C_2H_4O_5S$ |
| 9 | 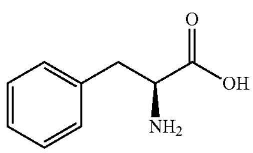 [SMILES: N[C@@H](Cc1ccccc1)C(=O)O] | Phenylalanine | $C_9H_{11}NO_2$ |
| 11 | 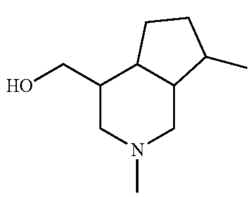 | (2,7-Dimethyloctahydro-1H-cyclopenta[c]pyridin-4-yl)methanol | $C_{11}H_{21}NO$ |
| 13 | 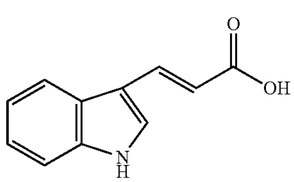 [SMILES: O=C(O)/C=C/c1c[nH]c2ccccc12] | Trans-3-indoleacrylic acid | $C_{11}H_9NO_2$ |
| 14 | 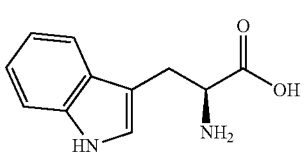 [SMILES: N[C@@H](Cc1c[nH]c2ccccc12)C(=O)O] | DL-Tryptophan | $C_{11}H_{12}N_2O_2$ |

TABLE 1B-continued

| NO. | Structure | Name | Formula |
|---|---|---|---|
| 16 | 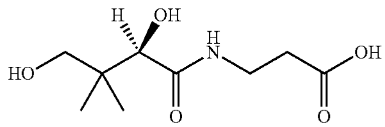 | Pantothenic acid | $C_9H_{17}NO_5$ |
| 28 | 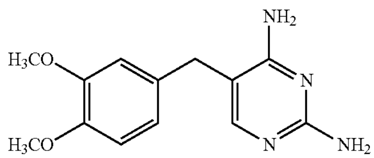 [SMILES: COc1ccc(Cc2cnc(N)nc2N)cc1OC] | Diaveridine | $C_{13}H_{16}N_4O_2$ |
| 29 | 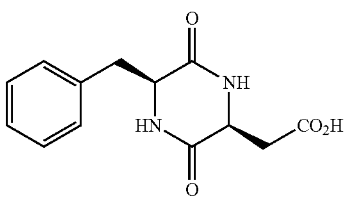 [SMILES: O=C(O)C[C@@H]1NC(=O)[C@H](Cc2ccccc2)NC1=O] | 5-Benzyl-3,6-dioxo-2-piperazinyl)acetic acid | $C_{13}H_{14}N_2O_4$ |
| 36 | 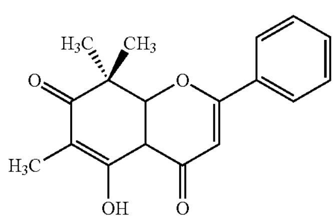 | Dasytrichone | $C_{18}H_{16}O_4$ |

Non-limiting examples of non-pregnancy biomarkers that can be utilized in a method of the disclosure are shown below in TABLE 2A and TABLE 2B. TABLE 2A shows details on biomarker chemical formulas, molecular weight, time, and MS fragmentation list. TABLE 2B shows corresponding chemical structures of compounds listed in TABLE 1A.

TABLE 2A

| NO. | Name | Formula | Molecular Weight | RT [min] | Fragmentation list |
|---|---|---|---|---|---|
| 1 | — | $C_6H_{11}NO$ | 113.08393 | 7.369 | 53.3, 54.2, 54.8, 55.9, 56.9, 57.9, 58.7, 59.8, 60.8, 64.9, 65.7, 66.9, 68.0, 69.0, 69.9, 70.9, 71.9, 72.8, 76.1, 76.8, 79.0, 80.8, 81.4, 84.0, 86.1, 90.9, 95.0, 96.1, 97.0, 105.0, 108.6, 111.9, 114.0 |
| 2 | Indole | $C_8H_7N$ | 117.0577 | 6.764 | 52.7, 54.8, 55.9, 57.1, 57.9, 58.8, 59.6, 60.7, 62.0, 65.1, 66.9, 67.9, 68.7, 70.0, 72.0, 72.7, 73.9, 76.1, 76.9, 87.0, 88.1, 90.1, 90.8, 94.8, 100.0, 102.2, 105.0, 112.8, 117.2, 118.1 |
| 3 | | $C_7H_{13}NO$ | 127.09957 | 8.006 | — |
| 4 | Leucoline | $C_9H_7N$ | 129.05774 | 6.78 | 50.8, 55.8, 60.8, 66.8, 76.9, 79.0, |

TABLE 2A-continued

| NO. | Name | Formula | Molecular Weight | RT [min] | Fragmentation list |
|---|---|---|---|---|---|
| | | | | | 84.0, 86.2, 88.0, 95.0, 101.0, 102.0, 103.0, 104.2, 105.0, 105.7, 117.9, 120.0, 128.0, 129.2, 130.1 |
| 5 | Skatole | $C_9H_9N$ | 131.07342 | 6.785 | 57.8, 61.1, 69.0, 72.0, 76.9, 78.9, 86.0, 90.0, 96.2, 97.0, 98.9, 103.8, 105.0, 106.2, 114.6, 117.0, 121.9, 129.9, 131.3, 132.0 |
| 6 | 6-Hydroxycaproic acid | $C_6H_{12}O_3$ | 132.07855 | 7.045 | 56.9, 69.9, 74.0, 76.8, 88.0, 91.1, 107.7, 122.9, 133.2 |
| 7 | 1,2,6-Hexanetriol | $C_6H_{14}O_3$ | 134.09407 | 5.774 | 52.9, 55.4, 56.1, 56.8, 60.8, 68.9, 72.9, 74.9, 78.9, 80.1, 88.8, 91.0, 92.8, 97.0, 105.0, 107.0, 116.9, 119.0, 122.9, 124.9, 129.9, 133.0, 135.0 |
| 8 | — | $C_4H_{11}O_3P$ | 138.04419 | 7.038 | 50.9, 52.9, 54.8, 56.8, 57.8, 58.8, 60.7, 62.8, 64.0, 64.9, 66.8, 67.7, 68.8, 71.1, 72.9, 74.8, 77.0, 77.7, 78.8, 79.8, 80.9, 82.1, 83.1, 91.0, 91.9, 93.1, 93.8, 95.0, 97.1, 97.9, 98.7, 100.1, 101.0, 104.2, 105.1, 108.9, 111.2, 111.9, 114.9, 115.9, 116.8, 118.9, 121.0, 124.8, 136.9, 139.0 |
| 9 | Naphthalen-2-amine | $C_{10}H_9N$ | 143.07328 | 6.749 | 54.7, 56.1, 56.8, 57.8, 58.7, 61.9, 62.6, 70.0, 70.8, 72.9, 74.8, 75.9, 76.8, 78.8, 80.1, 84.9, 85.9, 86.9, 88.9, 90.3, 98.0, 100.0, 100.9, 101.7, 102.9, 103.9, 105.0, 108.4, 113.0, 115.0, 116.0, 116.9, 118.0, 118.8, 120.9, 121.6, 128.2, 128.9, 133.0, 134.1, 138.8, 140.1, 144.1 |
| 10 | 8-Hydroxyquinoline | $C_9H_7NO$ | 145.05263 | 6.774 | 54.9, 55.9, 57.7, 60.0, 63.8, 64.8, 72.0, 72.9, 74.0, 74.8, 82.2, 86.1, 88.1, 90.1, 91.0, 94.9, 95.8, 96.8, 100.0, 101.0, 108.8, 116.9, 118.1, 118.8, 119.4, 120.9, 122.2, 128.0, 128.9, 129.8, 133.6, 146.1 |

TABLE 2A-continued

| NO. | Name | Formula | Molecular Weight | RT [min] | Fragmentation list |
|---|---|---|---|---|---|
| 11 | — | $C_6H_{14}O_4$ | 150.0891 | 7.036 | 54.9, 56.8, 64.8, 65.9, 68.8, 70.2, 73.1, 75.0, 75.5, 85.9, 87.0, 87.9, 88.9, 104.9, 114.9, 118.7, 131.8, 132.9 |
| 12 | — | $C_4H_8N_6O$ | 156.076 | 5.79 | 54.9, 56.6, 68.9, 69.7, 70.9, 72.7, 74.9, 80.9, 90.9, 92.9, 94.8, 106.0, 111.1, 113.7, 115.9, 117.7, 119.2, 124.8, 131.6, 143.2, 157.0 |
| 13 | 2,2,6,6-Tetramethyl-4-piperidinol | $C_9H_{19}NO$ | 157.14657 | 1.955 | 52.7, 54.9, 55.9, 56.9, 57.9, 58.8, 59.9, 62.0, 64.8, 65.9, 66.9, 69.0, 69.9, 71.0, 71.8, 72.6, 74.0, 74.9, 75.8, 77.0, 79.0, 81.0, 83.1, 84.1, 84.9, 85.9, 86.8, 88.0, 91.0, 91.7, 93.1, 93.9, 95.1, 96.0, 97.0, 98.4, 100.1, 102.1, 104.8, 108.1, 112.0, 112.9, 114.1, 115.0, 115.9, 116.8, 121.8, 123.0, 125.0, 130.0, 130.9, 138.0, 139.9, 140.8, 141.9, 143.0, 148.8, 157.1, 158.0 |
| 14 | 1,5-Naphthalenediamine | $C_{10}H_{10}N_2$ | 158.08414 | 6.777 | 55.9, 56.8, 61.0, 64.9, 65.9, 66.6, 71.9, 72.8, 74.8, 87.1, 88.9, 89.9, 91.0, 97.2, 102.8, 107.8, 113.9, 115.0, 115.8, 116.8, 117.7, 126.1, 128.7, 129.9, 131.1, 132.0, 136.0, 140.8, 142.0, 146.8, 158.9 |
| 15 | 1H-Indole-2-carboxylic acid | $C_9H_7NO_2$ | 161.04747 | 6.774 | 52.8, 55.8, 56.8, 57.8, 65.9, 67.8, 68.9, 70.0, 70.8, 71.8, 73.0, 74.8, 78.0, 78.9, 80.0, 81.8, 83.0, 83.9, 84.9, 85.9, 88.0, 90.8, 96.9, 97.9, 100.1, 100.9, 102.0, 103.7, 105.0, 106.0, 106.9, 108.9, 109.8, 113.0, 115.9, 118.3, 119.0, 120.3, 126.9, 129.2, 130.8, 138.8, 144.0, 145.0, 146.2, 147.0, 152.8, 155.4, 157.2, 162.0 |
| 16 | — | — | 165.07231 | 3.673 | 50.9, 53.7, 64.7, 68.1, 72.9, 73.9, 75.0, 77.0, 77.7, |

TABLE 2A-continued

| NO. | Name | Formula | Molecular Weight | RT [min] | Fragmentation list |
|---|---|---|---|---|---|
| | | | | | 79.0, 80.0, 84.6, 91.0, 92.0, 93.0, 94.1, 95.0, 102.4, 103.1, 103.9, 104.9, 107.0, 117.1, 118.0, 119.4, 120.0, 120.7, 123.9, 130.3, 131.0, 138.0, 149.2, 165.9 |
| 17 | — | $C_6H_{15}O_3P$ | 166.07585 | 3.69 | 54.9, 56.8, 58.8, 63.0, 66.9, 72.8, 74.9, 77.0, 77.9, 78.9, 80.0, 80.9, 82.1, 83.0, 84.9, 91.0, 92.0, 93.0, 94.1, 95.0, 96.0, 98.8, 102.3, 103.0, 104.1, 105.1, 105.9, 106.9, 108.0, 109.0, 111.2, 116.1, 117.1, 118.0, 119.1, 120.0, 121.0, 121.9, 125.0, 131.1, 132.2, 143.9, 145.0, 149.0, 151.1, 166.2, 167.0 |
| 18 | — | $C_8H_{16}O_4$ | 176.10479 | 7.035 | 56.7, 57.7, 66.6, 70.8, 72.7, 74.8, 79.9, 82.9, 84.9, 86.8, 90.9, 92.8, 95.0, 98.9, 100.8, 103.1, 104.2, 110.9, 112.9, 114.9, 116.0, 116.9, 118.9, 121.0, 130.1, 131.0, 131.7, 132.8, 135.0, 135.8, 137.2, 139.0, 139.7, 148.9, 149.5, 165.1, 171.0, 177.1 |
| 19 | (E)-Dacarbazine | $C_6H_{10}N_6O$ | 182.09163 | 6.692 | 51.9, 52.7, 54.8, 56.9, 63.7, 65.0, 67.0, 67.9, 69.7, 70.9, 72.9, 78.9, 80.8, 81.4, 83.1, 84.9, 90.9, 92.9, 94.9, 97.1, 97.9, 98.9, 99.8, 101.2, 105.0, 108.9, 113.9, 115.0, 116.9, 118.9, 121.7, 123.1, 124.8, 127.0, 128.0, 128.7, 130.0, 131.9, 133.0, 135.3, 137.0, 137.9, 139.0, 140.0, 141.6, 142.9, 144.9, 146.8, 152.9, 155.1, 156.9, 164.6, 165.3, 171.0, 181.2, 183.1 |
| 20 | — | $C_{11}H_{21}NO$ | 183.16201 | 8.000 | 54.9, 57.0, 57.8, 59.7, 66.9, 68.9, 72.0, 78.1, 80.9, 82.0, 82.8, 83.9, 90.9, 94.4, 95.2, |

TABLE 2A-continued

| NO. | Name | Formula | Molecular Weight | RT [min] | Fragmentation list |
|---|---|---|---|---|---|
| | | | | | 97.8, 99.1, 99.7, 110.4, 113.0, 113.7, 115.1, 116.2, 117.0, 117.9, 118.9, 128.0, 129.0, 130.8, 132.9, 139.7, 142.9, 143.7, 146.8, 148.8, 149.9, 153.7, 155.7, 172.0, 183.9 |
| 21 | Dinitrosopentamethylenetetramine | $C_5H_{10}N_6O_2$ | 186.08651 | 2.892 | 56.8, 60.8, 67.0, 70.9, 72.8, 74.8, 83.0, 87.9, 90.1, 90.8, 92.9, 94.8, 100.0, 108.9, 112.9, 113.9, 114.8, 118.9, 129.0, 130.9, 132.0, 133.9, 142.0, 148.0, 159.8, 162.9 |
| 22 | — | $C_{11}H_9NO_2$ | 187.06305 | 6.768 | 54.4, 55.9, 56.9, 64.9, 65.8, 70.0, 70.8, 72.9, 73.5, 74.9, 76.9, 80.8, 83.1, 85.7, 88.1, 88.9, 90.1, 91.0, 95.1, 95.9, 97.1, 98.9, 100.8, 102.9, 103.8, 104.7, 108.9, 111.0, 112.1, 113.9, 115.0, 116.0, 117.0, 118.0, 118.9, 119.9, 127.0, 127.9, 128.8, 129.9, 130.9, 132.0, 132.9, 133.9, 134.9, 136.6, 140.0, 142.0, 143.0, 144.0, 145.0, 146.0, 146.9, 147.6, 148.9, 150.7, 154.9, 156.6, 159.9, 160.9, 162.8, 164.9, 165.6, 169.9, 170.7, 188.0 |
| 23 | 5-Hydroxyindole-3-acetic acid | $C_{10}H_9NO_3$ | 191.05794 | 6.774 | 55.8, 56.7, 57.6, 64.9, 65.9, 68.8, 69.7, 71.0, 72.8, 74.0, 74.8, 77.1, 80.8, 82.2, 86.9, 87.9, 88.9, 90.9, 91.8, 93.1, 93.8, 98.8, 100.0, 100.8, 102.9, 103.7, 104.9, 106.1, 106.9, 108.9, 114.9, 115.9, 116.8, 117.9, 118.8, 119.9, 121.0, 129.9, 131.1, 131.9, 132.8, 134.0, 134.8, 136.3, 136.9, 141.0, 146.0, 146.9, 148.9, 149.9, 151.0, 151.9, 153.1, 160.8, |

TABLE 2A-continued

| NO. | Name | Formula | Molecular Weight | RT [min] | Fragmentation list |
|---|---|---|---|---|---|
| | | | | | 161.9, 164.0, 167.2, 168.9, 178.8, 187.0, 192.0 |
| 24 | — | $C_8H_{18}O_5$ | 194.11523 | 7.046 | 52.8, 56.9, 59.0, 71.0, 72.9, 74.9, 76.9, 78.9, 79.9, 81.3, 85.1, 89.0, 89.9, 90.9, 91.9, 93.0, 93.9, 95.2, 97.9, 98.8, 100.8, 104.0, 105.0, 106.1, 107.1, 108.2, 109.0, 111.0, 112.2, 113.0, 114.8, 115.9, 116.8, 119.1, 121.1, 123.8, 128.8, 131.1, 134.2, 135.1, 136.0, 137.0, 138.0, 138.9, 141.1, 141.9, 146.7, 148.8, 150.8, 151.9, 153.1, 153.8, 163.2, 164.9, 166.8, 181.0, 182.8, 195.0 |
| 25 | 3-Amino-5,7-dimethyl-1-adamantanol | $C_{12}H_{21}NO$ | 195.16204 | 7.28 | 57.8, 58.5, 59.2, 60.0, 63.8, 69.0, 72.9, 77.2, 78.9, 79.9, 80.9, 81.9, 85.0, 85.9, 93.2, 94.2, 95.1, 98.9, 104.8, 106.9, 109.0, 114.9, 115.6, 117.0, 119.2, 119.9, 121.4, 125.0, 126.8, 130.8, 132.0, 134.9, 136.8, 138.0, 139.2, 140.0, 142.0, 142.9, 144.8, 149.9, 152.8, 154.8, 155.6, 158.8, 159.7, 165.9, 167.0, 167.9, 173.0, 196.2 |
| 26 | — | $C_8H_{19}N_5O$ | 201.15921 | 1.958 | 52.9, 53.6, 54.9, 55.8, 56.9, 57.9, 58.9, 60.0, 61.9, 62.7, 65.1, 66.9, 67.7, 68.9, 70.0, 70.9, 71.9, 79.0, 81.0, 81.9, 83.0, 84.0, 85.0, 85.6, 88.1, 89.9, 92.8, 95.0, 95.8, 97.1, 99.9, 102.0, 103.0, 108.2, 111.0, 114.1, 116.1, 121.3, 123.1, 128.0, 141.1, 142.0, 146.0, 154.1, 183.9, 201.1, 202.2, 202.8 |
| 27 | 11-Aminoundecanoic acid | $C_{11}H_{23}NO_2$ | 201.17262 | 10.058 | 56.9, 58.0, 61.9, 83.0, 85.9, 88.0, 99.0, 100.1, 102.1, 111.1, 114.8, 117.0, 124.7, 130.0, |

TABLE 2A-continued

| NO. | Name | Formula | Molecular Weight | RT [min] | Fragmentation list |
|---|---|---|---|---|---|
| 28 | — | — | 201.18091 | 1.959 | 132.9, 142.1, 145.9, 149.9, 160.8, 171.9, 183.9, 202.1 54.9, 55.8, 56.9, 57.9, 58.9, 59.8, 61.9, 62.8, 64.2, 65.0, 66.9, 69.1, 69.9, 70.9, 71.9, 79.0, 81.0, 81.9, 83.0, 84.0, 84.9, 87.9, 90.0, 94.9, 97.1, 97.9, 102.1, 103.1, 110.1, 113.9, 116.8, 121.0, 123.1, 128.1, 139.7, 140.9, 142.0, 145.3, 146.1, 183.9, 202.1, 202.9 |
| 29 | — | — | 201.18741 | 1.943 | 52.9, 53.6, 54.9, 55.8, 56.9, 57.9, 58.9, 60.0, 61.9, 62.7, 65.1, 66.9, 67.7, 68.9, 70.0, 70.9, 71.9, 79.0, 81.0, 81.9, 83.0, 84.0, 85.0, 85.6, 88.1, 89.9, 92.8, 95.0, 95.8, 97.1, 99.9, 102.0, 103.0, 108.2, 111.0, 114.1, 116.1, 121.3, 123.1, 128.0, 141.1, 142.0, 146.0, 154.1, 183.9, 201.1, 202.2, 202.8 |
| 30 | — | $C_{11}H_{12}N_2O_2$ | 204.08954 | 6.769 | 54.9, 64.9, 73.9, 78.0, 78.9, 81.0, 91.0, 91.8, 94.7, 102.8, 103.9, 105.1, 107.1, 109.2, 109.9, 115.0, 116.0, 117.0, 118.0, 118.9, 120.1, 121.2, 126.9, 127.9, 129.0, 130.0, 130.9, 132.0, 133.0, 134.0, 134.9, 136.5, 140.2, 141.4, 142.0, 143.0, 144.0, 145.1, 146.0, 146.6, 147.8, 148.9, 153.5, 154.9, 158.0, 159.0, 160.0, 160.6, 169.0, 170.0, 170.7, 177.0, 188.0, 190.2, 205.1 |
| 31 | Kynurenine | $C_{10}H_{12}N_2O_3$ | 208.08442 | 6.787 | 56.9, 58.8, 60.8, 67.0, 69.0, 69.9, 70.8, 73.8, 78.9, 85.0, 91.0, 92.0, 94.0, 95.1, 97.0, 99.0, 103.9, 105.0, 105.7, 114.9, 117.0, 118.1, 118.8, 120.0, 121.0, 122.0, 122.9, |

TABLE 2A-continued

| NO. | Name | Formula | Molecular Weight | RT [min] | Fragmentation list |
|---|---|---|---|---|---|
| | | | | | 124.9, 126.7, 128.6, 130.0, 131.3, 132.0, 132.9, 134.8, 136.0, 137.0, 142.9, 145.0, 146.0, 146.9, 149.0, 149.9, 152.9, 157.8, 161.0, 162.0, 165.1, 166.1, 167.9, 171.3, 173.0, 173.9, 208.9 |
| 32 | — | $C_8H_7N_3O_4$ | 209.04265 | 3.603 | — |
| 33 | — | $C_7H_{10}N_6O_2$ | 210.08653 | 7.637 | — |
| 34 | — | $C_6H_{10}N_6O_3$ | 214.08142 | 2.899 | 50.8, 56.8, 66.9, 68.8, 69.7, 70.9, 74.1, 76.7, 77.8, 78.9, 80.9, 83.3, 84.8, 90.9, 92.9, 94.9, 95.9, 104.9, 105.9, 107.0, 111.0, 115.0, 116.1, 116.8, 120.9, 123.3, 133.0, 142.0, 157.8, 159.3, 168.8, 215.1 |
| 35 | — | $C_{12}H_{25}NO_2$ | 215.18832 | 2.988 | 57.8, 58.7, 70.1, 72.7, 76.0, 77.3, 81.0, 84.1, 85.0, 92.8, 95.0, 100.4, 102.2, 112.9, 116.1, 122.1, 123.0, 128.1, 142.8, 146.9, 157.0, 159.9, 172.0, 174.1, 206.8 |
| 36 | — | $C_{11}H_{23}NO_3$ | 217.16748 | 2.638 | — |
| 37 | — | $C_{11}H_{22}ClNO$ | 219.13869 | 5.155 | — |
| 38 | N-Hydroxy-L-tryptophan | $C_{11}H_{12}N_2O_3$ | 220.08447 | 6.753 | 56.8, 73.9, 81.1, 92.8, 93.7, 103.7, 104.9, 109.0, 111.0, 117.9, 120.8, 123.6, 127.9, 130.0, 131.9, 133.8, 135.7, 137.2, 145.9, 147.0, 148.0, 156.1, 156.9, 158.0, 163.3, 175.0, 176.3, 177.3, 178.0, 203.0 |
| 39 | 2-(Methylamino)-1H-benzo[de]isoquinoline-1,3(2H)-dione | $C_{13}H_{10}N_2O_2$ | 226.07154 | 6.764 | 54.8, 56.9, 67.1, 69.0, 70.7, 71.7, 78.8, 81.2, 83.0, 91.3, 92.5, 93.1, 94.8, 95.7, 97.0, 99.9, 100.8, 107.0, 109.1, 110.0, 110.9, 111.9, 113.4, 115.0, 116.0, 121.1, 122.7, 128.4, 131.2, 134.2, 137.0, 138.9, 140.9, 143.2, 148.9, 150.9, 152.9, 154.7, 157.0, 164.9, 167.0, 168.0, 169.9, 171.0, 173.7, 178.9, 181.7, |

TABLE 2A-continued

| NO. | Name | Formula | Molecular Weight | RT [min] | Fragmentation list |
|-----|------|---------|------------------|----------|--------------------|
| | | | | | 183.0, 184.2, 185.2, 191.3, 197.0, 226.9 |
| 40 | — | $C_6H_8N_6O_4$ | 228.06053 | 4.957 | 51.7, 52.9, 56.8, 80.9, 98.9, 105.0, 106.8, 108.8, 111.2, 114.9, 116.9, 118.2, 118.9, 120.8, 122.0, 122.9, 124.9, 129.1, 130.0, 130.9, 133.0, 135.0, 136.9, 137.6, 139.0, 140.9, 142.9, 143.7, 144.4, 147.0, 148.9, 150.8, 151.5, 152.9, 154.1, 154.9, 155.6, 156.9, 157.9, 158.8, 160.9, 162.7, 166.0, 167.2, 168.1, 168.9, 169.7, 170.6, 172.0, 173.0, 175.7, 179.0, 180.9, 191.1, 199.0, 208.9, 229.2 |
| 41 | — | $C_{10}H_{16}N_2O_2S$ | 228.09711 | 7.593 | 53.0, 56.7, 70.3, 78.9, 80.9, 81.8, 90.8, 94.1, 95.0, 97.0, 97.9, 98.9, 101.0, 104.9, 106.8, 111.0, 113.9, 114.7, 115.9, 116.9, 118.0, 118.9, 121.1, 123.0, 124.9, 126.7, 128.8, 129.8, 130.9, 132.9, 134.9, 136.8, 138.9, 139.9, 141.0, 142.0, 142.9, 143.6, 145.0, 146.1, 147.1, 148.9, 150.9, 153.0, 154.1, 154.9, 155.8, 156.9, 157.6, 159.1, 159.9, 161.0, 162.8, 168.9, 169.5, 172.9, 174.9, 175.9, 178.9, 181.0, 186.9, 187.9, 198.1, 198.8, 199.5, 209.1, 210.9 |
| 42 | — | $C_7H_{14}N_6O_3$ | 230.11263 | 7.935 | 54.9, 56.9, 69.0, 79.1, 82.2, 82.8, 95.0, 96.7, 99.0, 101.0, 104.1, 112.6, 113.9, 117.0, 118.9, 122.1, 125.8, 127.7, 129.0, 130.3, 131.6, 132.9, 135.0, 138.6, 140.7, 143.0, 144.1, 145.0, 145.6, 152.6, 155.1, |

TABLE 2A-continued

| NO. | Name | Formula | Molecular Weight | RT [min] | Fragmentation list |
|---|---|---|---|---|---|
| | | | | | 156.2, 156.8, 158.1, 158.9, 160.9, 169.0, 170.2, 170.9, 173.0, 174.9, 181.0, 182.9, 200.9 |
| 43 | — | $C_6H_{12}N_6O_4$ | 232.09199 | 2.88 | 56.8, 66.9, 68.9, 71.4, 74.0, 76.9, 78.0, 83.0, 85.1, 92.9, 95.2, 96.2, 98.0, 105.0, 106.1, 109.0, 113.9, 115.7, 123.3, 132.9, 135.0, 140.8, 141.9, 146.1, 185.2, 197.9, 215.2 |
| 44 | — | — | 232.80632 | 7.033 | — |
| 45 | — | $C_5H_{13}N_6O_3P$ | 236.07933 | 6.767 | 56.8, 67.2, 70.9, 72.7, 74.0, 74.9, 83.1, 91.1, 92.2, 93.2, 93.8, 94.9, 97.3, 97.9, 99.0, 101.9, 104.8, 109.0, 112.9, 114.9, 118.0, 119.6, 128.0, 130.0, 130.9, 131.9, 135.8, 139.2, 142.1, 143.9, 145.1, 146.0, 146.8, 147.9, 149.0, 153.2, 155.9, 157.0, 158.8, 162.9, 164.0, 165.0, 166.7, 170.0, 174.0, 176.9, 177.9, 184.9, 190.9, 200.1, 237.0 |
| 46 | — | $C_{10}H_{22}O_6$ | 238.14122 | 7.044 | 52.8, 56.9, 58.8, 62.8, 68.9, 71.0, 73.0, 73.9, 80.9, 84.1, 84.9, 87.0, 88.9, 89.8, 90.9, 102.0, 105.0, 107.0, 113.0, 116.2, 117.3, 118.0, 119.0, 129.7, 130.9, 132.3, 133.0, 133.9, 134.9, 143.7, 145.8, 147.7, 148.8, 152.8, 154.5, 162.8, 165.0, 175.8, 177.0, 194.8 |
| 47 | — | — | 238.14871 | 7.023 | 57.0, 59.1, 61.0, 65.3, 68.8, 73.0, 87.0, 88.9, 89.8, 93.1, 103.1, 107.0, 109.3, 112.0, 112.7, 115.9, 117.1, 130.9, 133.0, 133.8, 134.8, 148.9, 153.2, 165.8, 176.9, 178.0, 195.1 |
| 48 | — | — | 238.14992 | 7.028 | 59.0, 60.9, 72.9, 83.7, 87.1, 88.2, 89.0, 90.0, 91.0, 91.9, 102.9, |

TABLE 2A-continued

| NO. | Name | Formula | Molecular Weight | RT [min] | Fragmentation list |
|---|---|---|---|---|---|
| | | | | | 108.8, 112.8, 116.1, 117.1, 118.0, 129.9, 130.7, 131.5, 132.9, 134.0, 135.1, 145.9, 148.9, 151.0, 152.6, 161.1, 163.0, 164.7, 165.8, 167.0, 167.8, 170.4, 176.8 |
| 49 | — | $C_9H_{22}N_2O_5$ | 238.15322 | 6.984 | 57.0, 59.1, 61.0, 65.3, 68.8, 73.0, 87.0, 88.9, 89.8, 93.1, 103.1, 107.0, 109.3, 112.0, 112.7, 115.9, 117.1, 130.9, 133.0, 133.8, 134.8, 148.9, 153.2, 165.8, 176.9, 178.0, 195.1 |
| 50 | — | — | 239.14699 | 6.919 | 73.1, 73.7, 83.9, 87.9, 89.0, 90.0, 117.8, 122.1, 130.1, 132.0, 132.8, 134.0, 147.8, 150.3, 155.9, 170.2, 177.9, 182.0 |
| 51 | — | $C_8H_{12}N_6O_3$ | 240.09696 | 3.216 | — |
| 52 | — | $C_{12}H_{20}N_2O_3$ | 240.14766 | 7.145 | 57.8, 80.9, 88.2, 89.1, 90.9, 103.2, 107.9, 114.1, 116.8, 118.9, 119.7, 137.0, 151.9, 165.1, 181.4, 183.0, 191.2, 205.1, 224.3 |
| 53 | — | $C_6H_{14}N_2O_8$ | 242.07622 | 3.359 | — |
| 54 | — | $C_8H_{14}N_6O_3$ | 242.11243 | 7.367 | — |
| 55 | — | $C_9H_{12}N_6O_4$ | 244.092 | 4.402 | 56.9, 78.9, 94.9, 97.9, 105.9, 117.0, 131.9, 141.8, 144.8, 148.7, 152.9, 155.8, 164.7, 170.9, 179.7, 188.6, 196.9 |
| 56 | 5-Hydroxy-N-formylkynurenine | $C_{11}H_{12}N_2O_5$ | 252.07419 | 6.767 | 56.8, 58.8, 66.8, 68.9, 70.9, 77.1, 79.3, 80.9, 82.8, 85.0, 85.8, 87.0, 88.9, 95.0, 96.9, 99.0, 101.8, 103.0, 103.7, 105.1, 107.0, 109.0, 113.0, 115.0, 116.1, 117.0, 118.9, 119.6, 120.9, 129.0, 131.0, 133.0, 133.6, 134.9, 137.0, 137.7, 140.9, 143.0, 145.4, 146.7, 149.0, 150.1, 150.9, 151.9, 153.0, 155.0, 156.1, 158.2, 159.0, 160.3, 160.9, 161.6, 164.8, 167.3, 170.9, |

TABLE 2A-continued

| NO. | Name | Formula | Molecular Weight | RT [min] | Fragmentation list |
|---|---|---|---|---|---|
| | | | | | 175.3, 176.8, 178.7, 186.9, 189.0, 194.6, 206.9, 253.0 |
| 57 | — | $C_{10}H_{20}O_7$ | 252.12046 | 7.31 | — |
| 58 | — | $C_8H_{18}N_2O_7$ | 254.11252 | 8.314 | — |
| 59 | — | — | 255.16795 | 2.895 | 55.8, 70.0, 70.9, 71.9, 72.8, 73.8, 74.7, 78.7, 81.1, 83.9, 86.1, 86.9, 87.9, 88.9, 89.7, 90.9, 91.8, 100.8, 101.9, 102.8, 103.7, 105.3, 106.1, 106.7, 107.9, 108.8, 111.9, 112.5, 114.0, 115.9, 116.9, 118.0, 118.9, 120.1, 120.7, 125.9, 126.8, 128.0, 129.9, 130.8, 131.8, 132.8, 133.9, 134.9, 136.0, 140.0, 141.0, 141.9, 143.8, 145.1, 145.9, 147.0, 147.9, 148.8, 151.0, 151.8, 152.9, 159.9, 162.0, 163.9, 164.9, 165.9, 167.6, 168.9, 175.9, 176.9, 177.9, 188.7, 207.7, 209.8 |
| 60 | — | $C_{12}H_{24}N_4S$ | 256.17125 | 7.054 | — |
| 61 | — | — | 257.19858 | 5.334 | 56.8, 68.9, 83.9, 102.0, 107.1, 109.5, 118.9, 122.9, 125.2, 128.1, 149.0, 153.3, 158.0, 160.8, 169.9, 176.1, 185.1, 194.1 |
| 62 | N-lauroylglycine | $C_{14}H_{27}NO_3$ | 257.19858 | 4.886 | 55.9, 56.9, 57.8, 81.3, 83.9, 85.1, 102.1, 123.3, 139.9, 143.7, 145.2, 176.0, 177.1, 181.0, 187.2, 250.7 |
| 63 | — | $C_9H_{18}N_4O_5$ | 262.12746 | 7.01 | — |
| 64 | — | — | 268.59456 | 2.059 | — |
| 65 | — | — | 269.18347 | 7.039 | — |
| 66 | — | $C_8H_{18}N_2O_8$ | 270.10737 | 7.978 | — |
| 67 | — | $C_{14}H_{16}N_2O_2S$ | 276.09734 | 6.995 | 56.9, 81.1, 84.5, 101.1, 107.2, 121.0, 126.9, 135.2, 151.1, 155.8, 174.8, 176.0, 177.0, 178.7, 205.5, 235.2, 277.0 |
| 68 | — | — | 276.29762 | 7.056 | 56.9, 132.8, 148.9, 156.9, 158.0, 162.5, 164.3, 174.8, 179.2 |
| 69 | — | $C_8H_{24}ClN_9$ | 281.18376 | 7.012 | — |
| 70 | — | — | 283.19892 | 7.043 | 63.0, 72.9, 87.1, 89.9, 89.9, 97.1, 107.2, 116.9, 133.0, 136.0, |

TABLE 2A-continued

| NO. | Name | Formula | Molecular Weight | RT [min] | Fragmentation list |
|---|---|---|---|---|---|
| 71 | — | $C_{14}H_{16}N_4O_3$ | 288.11788 | 3.909 | 151.1, 153.8, 176.9, 182.2, 195.0, 239.0 56.8, 94.9, 117.1, 119.4, 149.4, 154.9, 156.6, 171.0, 176.4, 181.0, 199.4, 289.1 |
| 72 | — | $C_4H_7N_2O_{11}P$ | 289.97981 | 1.338 | 68.9, 84.8, 91.0, 115.1, 142.9, 160.9, 165.0, 178.2, 187.2, 216.5 |
| 73 | — | $C_{10}H_{17}NO_7S$ | 295.07271 | 3.621 | — |
| 74 | — | $C_{18}H_{16}O_4$ | 296.10465 | 3.599 | 55.0, 56.9, 58.8, 64.9, 67.2, 70.8, 71.7, 75.0, 77.0, 78.9, 90.0, 91.0, 93.0, 94.9, 101.9, 103.0, 105.0, 107.1, 107.8, 111.0, 116.3, 121.0, 125.8, 131.2, 148.8, 150.9 |
| 75 | — | — | 297.17815 | 7.306 | 69.1, 71.2, 72.9, 87.4, 88.6, 102.9, 104.8, 113.1, 119.1, 131.0, 133.0, 157.7, 170.0, 173.5, 197.8 |
| 76 | — | $C_{17}H_{20}N_2OS$ | 300.11791 | 5.213 | 54.6, 109.2, 146.9, 154.7, 171.0, 177.0 |
| 77 | — | $C_{15}H_{27}NO_5$ | 301.18834 | 4.974 | 56.8, 58.0, 62.0, 75.0, 81.0, 83.9, 84.8, 102.0, 102.9, 114.0, 123.1, 128.0, 162.6, 166.8, 188.7 |
| 78 | — | $C_{10}H_{18}N_6O_5$ | 302.13353 | 4.086 | 57.0, 66.8, 72.9, 77.0, 84.6, 96.0, 96.8, 98.8, 114.9, 123.0, 131.0, 146.9, 148.7, 156.3, 159.6, 175.0, 177.3, 181.1, 211.0, 222.9, 303.1 |
| 79 | — | $C_{10}H_{16}O_7P_2$ | 310.03754 | 3.61 | — |
| 80 | — | — | 322.09363 | 7.05 | — |
| 81 | — | $C_{16}H_{29}NO_6$ | 331.1989 | 6.775 | — |
| 82 | — | $C_{20}H_{14}O_5$ | 334.08355 | 6.765 | 56.6, 129.9, 148.9, 173.9, 187.9, 191.7, 215.0, 217.3, 247.0 |
| 83 | — | $C_9H_{12}N_3O_9P$ | 337.03072 | 1.545 | 74.1, 100.8, 101.8, 117.2, 131.1, 133.8, 142.7, 145.8, 147.0, 147.9, 148.9, 155.8, 156.9, 160.9, 165.8, 169.8, 172.1, 174.3, 175.2, 176.2, 178.9, 181.0, 190.8, 201.1, 202.3, 280.3, 338.1 |
| 84 | — | $C_{18}H_{27}NO_3S$ | 337.17098 | 1.665 | 55.8, 67.9, 69.7, 72.8, 83.9, 85.8, 86.9, 87.8, 91.0, |

TABLE 2A-continued

| NO. | Name | Formula | Molecular Weight | RT [min] | Fragmentation list |
|---|---|---|---|---|---|
| | | | | | 101.9, 102.7, 107.7, 112.0, 113.8, 114.9, 115.8, 118.1, 130.0, 130.9, 131.8, 132.9, 133.8, 134.8, 137.8, 140.1, 144.0, 145.8, 147.1, 148.0, 148.9, 149.9, 150.7, 151.8, 155.9, 156.6, 157.7, 158.8, 159.6, 161.9, 163.9, 164.9, 165.8, 167.8, 171.9, 172.7, 173.9, 174.8, 175.8, 176.7, 177.9, 179.0, 179.8, 183.6, 190.1, 191.9, 201.8, 216.0, 219.8, 234.8, 238.0, 245.7 |
| 85 | — | $C_{15}H_{18}N_6O_5$ | 362.13355 | 4.884 | — |
| 86 | — | — | 393.09001 | 3.625 | — |
| 87 | — | — | 415.07206 | 3.62 | — |
| 88 | — | — | 432.10054 | 6.762 | — |
| 89 | — | $C_{24}H_{38}N_8$ | 438.32205 | 1.942 | 56.8, 62.0, 83.9, 85.0, 102.0, 123.0, 146.1, 202.1 |
| 90 | — | — | 698.41818 | 7.045 | — |
| 91 | — | $C_5H_{10}O_3$ | 118.0623 | 5.382 | 59.0, 71.0, 73.8, 74.8, 99.9, 116.9 |
| 92 | — | $C_1H_2S_1Br_1$ | 124.9087 | 24.875 | 78.7, 81.9, 87.9, 94.1, 105.9, 123.9 |
| 93 | — | $C_9H_{17}N_1O_5$ | 219.1099 | 3.968 | 70.8, 71.9, 87.9, 98.8, 116.1, 127.8, 146.1, 218.1 |
| 94 | — | $C_3H_3O_2S_2P_1Cl_2$ | 235.8662 | 1.938 | 58.9, 70.9, 73.8, 87.0, 89.0, 92.8, 94.7, 101.1, 103.0, 108.3, 110.5, 112.8, 117.0, 131.0, 133.2, 136.7, 144.7, 148.9, 152.5, 154.7, 160.6, 162.8, 171.1, 174.7, 176.9, 191.1, 234. |
| 95 | — | $C_{13}H_{14}N_2O_4$ | 262.0947 | 3.758 | 56.9, 57.8, 73.8, 84.1, 87.0, 92.8, 98.2, 102.8, 110.9, 116.0, 117.9, 124.8, 126.9, 128.0, 130.1, 131.0, 132.0, 132.8, 140.1, 141.0, 144.0, 146.0, 157.1, 157.9, 158.7, 170.6, 175.0, 192.8, 218.8 |
| 96 | — | $C_7H_{10}N_{10}O_2$ | 266.0995 | 2.646 | 79.0, 94.8, 99.0, 118.9, 121.1, 126.2, 135.1, 146.9, 160.9, 162.8, 174.8, |

TABLE 2A-continued
| NO. | Name | Formula | Molecular Weight | RT [min] | Fragmentation list |
|---|---|---|---|---|---|
| | | | | | 178.8, 191.0, 197.2 |
| 97 | — | $C_8H_{21}N_3O_4S_2$ | 287.0973 | 3.966 | 88.1, 99.1, 117.2, 146.0, 151.9, 154.0 |
| 98 | — | $C_{12}H_{10}N_6O_4$ | 302.0761 | 2.635 | 58.9, 88.7, 101.0, 108.8, 114.8, 118.8, 136.7, 147.0, 152.9, 156.8, 164.9, 174.8, 186.9, 209.0 |
| 99 | — | $C_{14}H_{30}O_5S_1$ | 310.1809 | 24.987 | 79.7, 80.7, 94.8, 97.0, 98.0, 104.8, 114.8, 117.0, 117.8, 122.9, 128.7, 130.9, 150.8, 154.8, 163.1, 167.2, 172.1, 173.2, 174.6, 182.9, 205.2, 209.0, 222.9, 309.1, 309.8 |
| 100 | — | $C_6H_{16}N_4O_1S_1$ | 312.105 | 2.638 | 58.9, 88.9, 91.1, 99.0, 119.0, 131.1, 134.8, 137.1, 146.9, 152.9, 163.1, 174.9, 180.7, 241.2, 244.8 |
| 101 | — | $C_7H_5O_{10}S_2P_3$ | 405.8534 | 24.829 | — |
| 102 | — | $C_5H_8N_6O_{14}S_1$ | 407.9821 | 20.335 | — |
TABLE 2B
| NO. | Structure | Name | Formula |
|---|---|---|---|
| 2 | 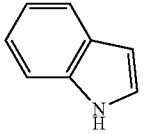 | Indole | $C_8H_7N$ |
| 4 | 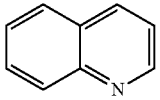 | Leucoline | $C_9H_7N$ |
| 5 | 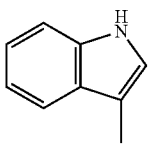 | Skatole | $C_9H_9N$ |
| 6 | 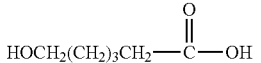 | 6-Hydroxycaproic acid | $C_6H_{12}O_3$ |
| 7 | 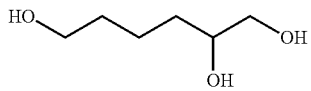 | 1,2,6-Hexanetriol | $C_6H_{14}O_3$ |
| 9 | 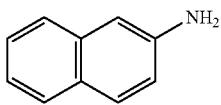 [SMILES: Nc1ccc2ccccc2c1] | Naphthalen-2-amine | $C_{10}H_9N$ |

TABLE 2B-continued

| NO. | Structure | Name | Formula |
|---|---|---|---|
| 10 | 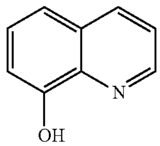 [SMILES: Oc1cccc2cccnc12] | 8-Hydroxyquinoline | $C_9H_7NO$ |
| 13 | 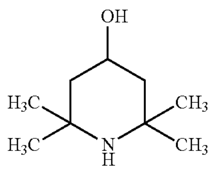 | 2,2,6,6-Tetramethyl-4-piperidinol | $C_9H_{19}NO$ |
| 14 | 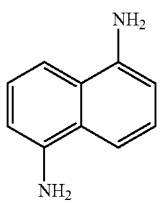 [SMILES: Nc1cccc2c(N)cccc12] | 1,5-Naphthalenediamine | $C_{10}H_{10}N_2$ |
| 15 | 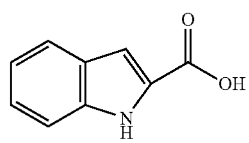 [SMILES: O=C(O)c1cc2ccccc2[nH]1] | 1H-Indole-2-carboxylic acid | $C_9H_7NO_2$ |
| 19 | 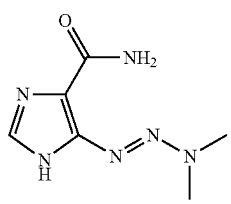 | (E)-Dacarbazine | $C_6H_{10}N_6O$ |
| 21 | 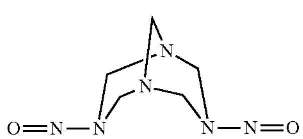 [SMILES: O=NN1CN2CN(C1)CN(N=O)C2] | Dinitrosopentamethylenetetramine | $C_5H_{10}N_6O_2$ |
| 23 | 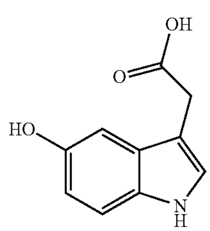 [SMILES: O=C(O)Cc1c[nH]c2ccc(O)cc12] | 5-Hydroxyindole-3-Acetic Acid | $C_{10}H_9NO_3$ |
| 25 | 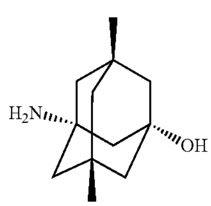 | 3-Amino-5,7-dimethyl-1-adamantanol | $C_{12}H_{21}NO$ |
| 27 | 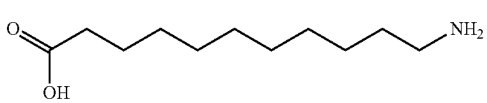 [SMILES: NCCCCCCCCCCC(=O)O] | 11-Aminoundecanoic acid | $C_{11}H_{23}NO_2$ |

TABLE 2B-continued
| NO. | Structure | Name | Formula |
|---|---|---|---|
| 31 | 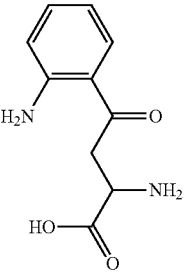 [SMILES: Nc1ccccc1C(=O)CC(N)C(=O)O] | Kynurenine | $C_{10}H_{12}N_2O_3$ |
| 38 | 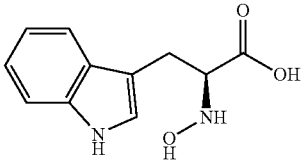 [SMILES: O=C(O)[C@H](Cc1c[nH]c2ccccc12)NO] | N-Hydroxy-L-tryptophan | $C_{11}H_{12}N_2O_3$ |
| 39 | 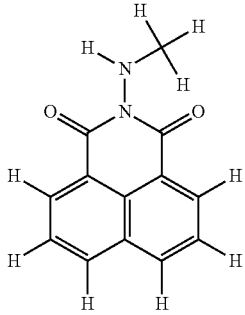 [SMILES: CNN1C(=O)c2cccc3cccc(c23)C1=O] | 2-(Methylamino)-1H-benzo[de]isoquinoline-1,3(2H)-dione | $C_{13}H_{10}N_2O_2$ |
| 56 | 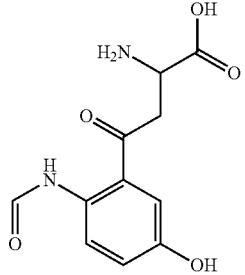 [SMILES: NC(CC(=O)c1cc(O)ccc1NC=O)C(=O)O] | 5-Hydroxy-N-formylkynurenine | $C_{11}H_{12}N_2O_5$ |
| 62 | 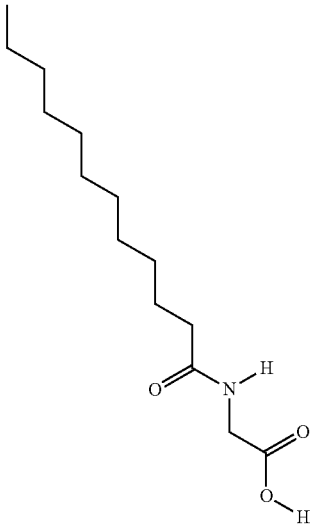 [SMILES: CCCCCCCCCCCC(=O)NCC(=O)O] | N-Lauroylglycine | $C_{14}H_{27}NO_3$ |

EXAMPLES

Example 1: Identification of Pregnancy and Non-Pregnancy Biomarkers

Sample Collection.

Embryo-conditioned Vitrolife media was collected on day 5 of culture following fertilization and frozen for storage at −20° C.

Sample Preparation

Frozen embryo-conditioned media was thawed at 4° C. overnight. A total of 20 μL of embryo-conditioned media was then added to 480 μL of HPLC grade water in Amicon® Ultra 0.5-mL 3-kDa centrifugal filters. Samples were then spun by centrifuge at 4,000×g for 10 min to separate proteins from metabolites. A schematic of this process is shown in FIG. 1. Following centrifugation, the metabolite fraction was present in the solution that passed through the Amicon® filter, while protein was present in the filter membrane. Both the metabolite fraction and protein extract were then separately collected and frozen at −80° C. for storage and future analysis.

Metabolomics Analysis by UPLC-Orbitrap Fusion Mass Spectroscopy

Untargeted metabolomics analysis was conducted using a Vanquish UPLC-Orbitrap Fusion Tribrid Mass Spectrometer (UPLC-OT-FTMS). Samples were passed through a 1.7-μm ACQUITY UPLC BEH C18 reverse phase column (Waters, 30 Å, 1.7 μm, 2.1 mm×100 mm) to an Orbitrap Fusion Tribrid Mass Spectrometer (Thermo Scientific) operated under both positive and negative modes via a heated ESI source. For the UPLC step, the following gradient was used: hold at 5% Eluent B (acetonitrile with 0.1% (v/v) formic acid) and 95% Eluent A (Milli-Q water with 0.1% (v/v) formic acid) for 2 min; ramp to 65% B, 35% A for 16 min; ramp to 100% B for 7 min and hold for 8 min. An 8 min column re-equilibration with the starting ratio of eluents was carried out between sample analyses. Throughout the process a flow rate of 0.2 mL/min and an injection volume of 20 μL were used.

For negative mode analysis, the ESI setting was 3,000 volts, 30 AU sheath gas, 10 AU Aux gas, 0 AU sweep gas, a 325° C. ion transfer tube temperature and a 200° C. vaporizer temperature. The Orbitrap full scan was run at 500,000 resolutions with a scan range 100-1000 m/z and radio frequency (RF) Lens at 40%. For $MS^2$, the isolation window was set at 0.7 m/z while performing both CID and HCD using an ion trap mass spectrometer as the detector. The automatic gain control (AGC) was set at 10,000 with an intensity threshold at 5,000.

Compound discoverer software 2.1 (Thermo Fisher) was used to identify the metabolomics compounds and to perform the multivariate analyses (Volcano plot, Principal Components Analysis (PCA), Partial Least Squares Discriminant Analysis (PLS-DA) and trend analysis). In brief, all the raw spectra were uploaded to the software, and retention times were aligned for all spectra. Mass features in each individual spectrum were then detected. The molecular formula for each peak was calculated with the following parameters: $C_{4-50}H_{4-200}O_{0-20}N_{0-8}S_{0-2}P_{0-2}$. Molecular formulas that are unlikely to occur in nature, or are not chemically possible, were then removed. For the natural abundance of $^{13}C$ relative to $^{12}C$, a value of 1.11% was used. For any compound containing phosphorous, a requirement that at least three oxygen atoms per each phosphorus atom must exist was set. Based on this analysis, compound formulas were assigned within 1 ppm error.

The normalized integrated area of mass spectra for each compound was used to perform volcano plots and trend analysis. De novo compound structure elucidation was identified based on MS/MS and confirmed using in silico fragmentation prediction software (e.g. Mass Frontier, MetFrag, and ACD/MS fragmenter).

Results of Biomarker Identification.

A total of 47 embryo-conditioned Vitrolife media samples were analyzed by liquid chromatography-MS (LC-MS). The media samples were separated into 3 groups based on known clinical outcomes: 1) not pregnant (NP; 17 samples), 2) pregnant (P; 20 samples), and 3) blank control media (C; 10 samples). Over 8,000 single chemical compounds were identified in conditioned media groups.

Figure 3:
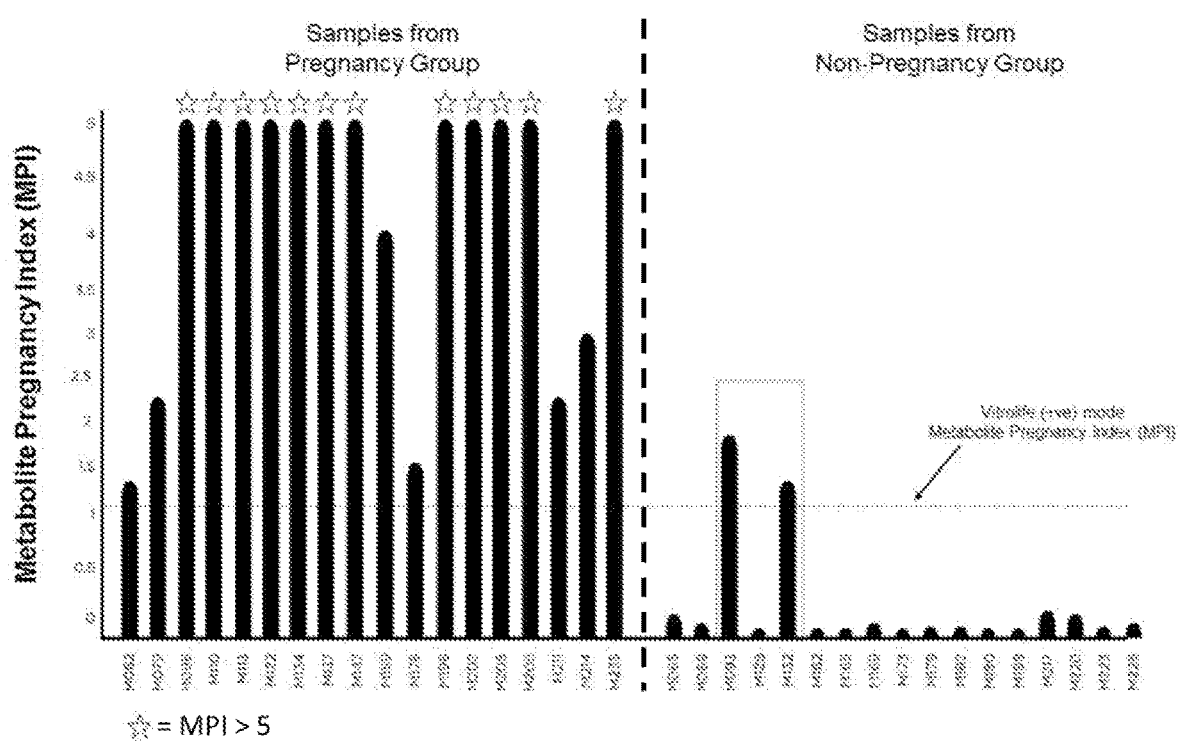
FIG. 3 shows pregnancy indices calculated for samples of conditioned media from embryos that did or did not result in pregnancy following transfer.

To identify metabolites that were differentially present in P vs. NP samples, the relative abundance of metabolites in P vs. NP samples was determined (in terms of fold change) and analyzed with volcano plots. This analysis was performed for results obtained with both positive mode and negative mode MS methods. As shown in FIG. 3 and TABLE 3, 154 potential biomarkers of pregnancy and non-pregnancy were identified. Cutoff values for the identification of a metabolite as a pregnancy or non-pregnancy biomarker are also shown in TABLE 3. Using the tandem MS methods described in the preceding section, details on the chemical name, molecular weight, chemical formula, retention time, fragmentation pattern, and/or chemical structure of pregnant and non-pregnant biomarkers were determined and are shown above in TABLES 1A, 1B, 2A, and 2B.

TABLE 3

| Media | Total number of biomarkers | Number of Biomarkers per mode | | Biomarker per class | | Cut-off −log2 FC | Cut-off −log10 p-value |
| --- | --- | --- | --- | --- | --- | --- | --- |
| Vitro-life | 154 | Positive | 126 | P | 36 | 1.00 | 2.00 |
| | | | | NP | 90 | −1.00 | 2.00 |
| | | Negative | 28 | P | 16 | 2.00 | 2.00 |
| | | | | NP | 12 | −2.00 | 2.00 |

FC = Fold change

Prediction of Implantation Probability.

Based on the relative abundances of pregnancy and non-pregnancy biomarkers in a conditioned-media sample, the probability of implantation success of the corresponding embryo can be assessed. To facilitate an assessment of embryo implantation success probability, a Metabolite Pregnancy Index (MPI) was developed. MPI is calculated by dividing the total integrated area of mass spectra peaks corresponding to selected pregnancy biomarkers by the total integrated area of mass spectra peaks corresponding to selected non-pregnancy biomarkers. MPI calculations can be based on the presence of anywhere from 1 to infinite numbers of pregnant/non-pregnant biomarkers. In the present example, a MPI was calculated based on the 154 identified biomarkers, and a pregnancy/non-pregnancy value of MPI=1.0 was set, with a MPI>1.0 indicating an embryo with a high probability of implantation success. Based on these parameters, results showed that 100% (20/20) of embryos that implanted (P samples) had a MPI>1.0. Of these 20 embryos, 8 had an MPI between 1-10 and 12 had an MPI>200. Of the embryos that did not implant (NP samples), 88% (15/17) had an MPI<1.0, while 12% (2/17) had an MPI from 1-2. The average MPI of NP samples was 0.068. These results are summarized in FIG. 3. From these results samples can be classified into three groups: 1) Those with a very high probability of implantation success (MPI>10), 2) those with a high probability of implantation success: (MPI from 1-10, and 3) those with a low probability of implantation success (MPI<1).

Embodiments

The following non-limiting embodiments provide illustrative examples of methods of the disclosure but do not limit the scope of methods of the disclosure.

Embodiment 1. A method comprising: a) measuring an amount of a metabolite in a sample of culture media in which an embryo has been cultured in vitro, wherein the metabolite is selected from the group consisting of caprolactam, N-cyclohexylformamide, threo-3-hydroxy-2-methylbutyric acid, sulfoacetic acid, (2,7-dimethyloctahydro-1H-cyclopenta[c]pyridin-4-yl)methanol, trans-3-indoleacrylic acid, pantothenic acid, diaveridine, (5-benzyl-3,6-dioxo-2-piperazinyl)acetic acid, dasytrichone, indole, leucoline, skatole, 6-hydroxycaproic acid, 1,2,6-hexanetriol, naphthalen-2-amine, 8-hydroxyquinoline, 2,2,6,6-tetramethyl-4-piperidinol, 1,5-naphthalenediamine, 1H-indole-2-carboxylic acid, (E)-dacarbazine, dinitrosopentamethylenetetramine, 5-hydroxyindole-3-acetic acid, 3-amino-5,7-dimethyl-1-adamantanol, 11-aminoundecanoic acid, kynurenine, N-hydroxy-L-tryptophan, 2-(methylamino)-1H-benzo[de]isoquinoline-1,3(2H)-dione, 5-hydroxy-N-formylkynurenine, and N-lauroylglycine; and b) assessing a likelihood of success of implantation of the embryo into a uterus upon introduction of the embryo into the uterus based at least partially on the amount of the metabolite present in the sample of culture media.

Embodiment 2. The method of embodiment 1, wherein the metabolite is carpolactam.

Embodiment 3. The method of embodiment 1, wherein the metabolite is N-cyclohexylformamide.

Embodiment 4. The method of embodiment 1, wherein the metabolite is threo-3-hydroxy-2-methylbutyric acid.

Embodiment 5. The method of embodiment 1, wherein the metabolite is sulfoacetic acid.

Embodiment 6. The method of embodiment 1, wherein the metabolite is (2,7-dimethyloctahydro-1H-cyclopenta[c]pyridin-4-yl)methanol.

Embodiment 7. The method of embodiment 1, wherein the metabolite is trans-3-indoleacrylic acid.

Embodiment 8. The method of embodiment 1, wherein the metabolite is pantothenic acid.

Embodiment 9. The method of embodiment 1, wherein the metabolite is diaveridine.

Embodiment 10. The method of embodiment 1, wherein the metabolite is (5-benzyl-3,6-dioxo-2-piperazinyl)acetic acid.

Embodiment 11. The method of embodiment 1, wherein the metabolite is dasytrichone, Embodiment 12. The method of embodiment 1, wherein the metabolite is indole.

Embodiment 13. The method of embodiment 1, wherein the metabolite is leucoline.

Embodiment 14. The method of embodiment 1, wherein the metabolite is skatole.

Embodiment 15. The method of embodiment 1, wherein the metabolite is 6-hydroxycaproic acid.

Embodiment 16. The method of embodiment 1, wherein the metabolite is 1,2,6-hexanetriol.

Embodiment 17. The method of embodiment 1, wherein the metabolite is naphthalen-2-amine.

Embodiment 18. The method of embodiment 1, wherein the metabolite is 8-hydroxyquinoline.

Embodiment 19. The method of embodiment 1, wherein the metabolite is 2,2,6,6-tetramethyl-4-piperidinol.

Embodiment 20. The method of embodiment 1, wherein the metabolite is 1,5-naphthalenediamine.

Embodiment 21. The method of embodiment 1, wherein the metabolite is 1H-indole-2-carboxylic acid.

Embodiment 22. The method of embodiment 1, wherein the metabolite is (E)-dacarbazine.

Embodiment 23. The method of embodiment 1, wherein the metabolite is dinitrosopentamethylenetetramine.

Embodiment 24. The method of embodiment 1, wherein the metabolite is 5-hydroxyindole-3-acetic acid.

Embodiment 25. The method of embodiment 1, wherein the metabolite is 3-amino-5,7-dimethyl-1-adamantanol.

Embodiment 26. The method of embodiment 1, wherein the metabolite is 11-aminoundecanoic acid.

Embodiment 27. The method of embodiment 1, wherein the metabolite is kynurenine.

Embodiment 28. The method of embodiment 1, wherein the metabolite is N-hydroxy-L-tryptophan.

Embodiment 29. The method of embodiment 1, wherein the metabolite is 2-(methylamino)-1H-benzo[de]isoquinoline-1,3(2H)-dione.

Embodiment 30. The method of embodiment 1, wherein the metabolite is 5-hydroxy-N-formylkynurenine.

Embodiment 31. The method of embodiment 1, wherein the metabolite is N-lauroylglycine.

Embodiment 32. A method comprising measuring an amount of each of a plurality of metabolites in a mixture, wherein each metabolite is one of the following compounds: (2,7-dimethyloctahydro-1H-cyclopenta[c]pyridin-4-yl) methanol, trans-3-indoleacrylic acid, pantothenic acid, diaveridine, (5-benzyl-3,6-dioxo-2-piperazinyl)acetic acid, dasytrichone, indole, skatole, 8-hydroxyquinoline, (E)-dacarbazine, kynurenine, or N-hydroxy-L-tryptophan.

Embodiment 33. The method of embodiment 32, wherein the mixture is a sample of culture media in which an embryo has been cultured in vitro.

Embodiment 34. The method of embodiment 32 or 33, further comprising assessing a likelihood of success of implantation of the embryo based on the amount of at least one metabolite in the mixture.

Embodiment 35. The method of any one of embodiments 32-34, further comprising measuring an amount of caprolactam in the mixture.

Embodiment 36. The method of any one of embodiments 32-35, further comprising measuring an amount of N-cyclohexylformamide in the mixture.

Embodiment 37. The method of any one of embodiments 32-36, further comprising measuring an amount of threo-3-hydroxy-2-methylbutyric acid in the mixture.

Embodiment 38. The method of any one of embodiments 32-37, further comprising measuring an amount of sulfoacetic acid in the mixture.

Embodiment 39. The method of any one of embodiments 32-38, further comprising measuring an amount of phenylalanine in the mixture.

Embodiment 40. The method of any one of embodiments 32-39, further comprising measuring an amount of DL-tryptophan in the mixture.

Embodiment 41. The method of any one of embodiments 32-40, further comprising measuring an amount of leucoline in the mixture.

Embodiment 42. The method of any one of embodiments 32-41, further comprising measuring an amount of 6-hydroxycaproic acid in the mixture.

Embodiment 43. The method of any one of embodiments 32-42, further comprising measuring an amount of 1,2,6-hexanetriol in the mixture.

Embodiment 44. The method of any one of embodiments 32-43, further comprising measuring an amount of naphthalen-2-amine in the mixture.

Embodiment 45. The method of any one of embodiments 32-44, further comprising measuring an amount of 8-hydroxyquinoline in the mixture.

Embodiment 46. The method of any one of embodiments 32-45, further comprising measuring an amount of 2,2,6,6-tetramethyl-4-piperidinol in the mixture.

Embodiment 47. The method of any one of embodiments 32-46, further comprising measuring an amount of 1,5-naphthalenediamine in the mixture.

Embodiment 48. The method of any one of embodiments 32-47, further comprising measuring an amount of 1H-indole-2-carboxylic acid in the mixture.

Embodiment 49. The method of any one of embodiments 32-48, further comprising measuring an amount of dinitrosopentamethylenetetramine in the mixture.

Embodiment 50. The method of any one of embodiments 32-49, further comprising measuring an amount of hydroxyindole-3-acetic acid in the mixture.

Embodiment 51. The method of any one of embodiments 32-50, further comprising measuring an amount of 3-amino-5,7-dimethyl-1-adamantanol in the mixture.

Embodiment 52. The method of any one of embodiments 32-51, further comprising measuring an amount of 11-aminoundecanoic acid in the mixture.

Embodiment 53. The method of any one of embodiments 32-52, further comprising measuring an amount of kynurenine in the mixture.

Embodiment 54. The method of any one of embodiments 32-53, further comprising measuring an amount of 2-(methylamino)-1H-benzo[de]isoquinoline-1,3(2H)-dione in the mixture.

Embodiment 55. The method of any one of embodiments 32-54, further comprising measuring an amount of 5-hydroxy-N-formylkynurenine in the mixture.

Embodiment 56. The method of any one of embodiments 32-55, further comprising measuring an amount of N-lauroylglycine in the mixture.

Embodiment 57. A method comprising: a) performing an assay to obtain a first set of mass spectra corresponding to a first metabolite present in a sample of culture media in which an embryo has been cultured in vitro ($ms_1$); b) using the first set of mass spectra to determine an amount of the first metabolite in the sample of culture media, wherein the amount of the first metabolite is associated with a low probability of embryo implantation success; c) performing an assay to obtain a second set of mass spectra corresponding to a second metabolite present in the sample of culture media in which the embryo has been cultured in vitro ($ms_2$); d) using the second set of mass spectra to determine an amount of the second metabolite, wherein the amount of the second metabolite is associated with a high probability of embryo implantation success; and comparing the amount of the first metabolite with the amount of the second metabolite.

Embodiment 58. The method of embodiment 57, wherein the amount of the first metabolite is compared to the amount of the second metabolite by solving the equation:

$$MPI = \frac{\int ms_2}{\int ms_1}.$$

Embodiment 59. The method of embodiment 57 or 58, further comprising determining an amount of each of 5 additional metabolites in the sample of culture media, wherein the 5 additional metabolites are associated with a low probability of embryo implantation success.

Embodiment 60. The method of any one of embodiments 57-59, further comprising determining an amount of each of 5 additional metabolites in the sample of culture media, wherein the 5 additional metabolites are associated with a high probability of embryo implantation success.

Embodiment 61. The method of any one of embodiments 57, 58, and 60, further comprising determining an amount of each of 19 additional metabolites in the sample of culture media, wherein the 19 additional metabolites are associated with a low probability of embryo implantation success.

Embodiment 62. The method of any one of embodiments 57-59 and 61, further comprising determining an amount of each of 12 additional metabolites in the sample of culture media, wherein the 12 additional metabolites are associated with a high probability of embryo implantation success.

Embodiment 63. The method of any one of embodiments 57, 58, 60, and 62, further comprising determining an amount of each of 19-93 additional metabolites in the sample of culture media, wherein the 19-93 additional metabolites are associated with a low probability of embryo implantation success.

Embodiment 64. The method of any one of embodiments 57-59, 61, and 63, further comprising determining an amount of each of 11-50 additional metabolites in the sample of culture media, wherein the 11-50 additional metabolites are associated with a high probability of embryo implantation success.

Embodiment 65. The method of any one of embodiments 57, 58, 60, 62, and 64, further comprising determining an amount of each of 19-101 additional metabolites in the sample of culture media, wherein the 19-101 additional metabolites are associated with a low probability of embryo implantation success.

Embodiment 66. The method of any one of embodiments 57-59, 61, 63, and 65, further comprising determining an amount of each of 11-51 additional metabolites in the sample of culture media, wherein the 11-51 additional metabolites are associated with a high probability of embryo implantation success.

Embodiment 67. A method comprising: a) measuring an amount of each of 4 metabolites in a sample of culture media in which an embryo has been cultured in vitro; and b) assessing a likelihood of success of implantation of the embryo into a uterus upon introduction of the embryo into the uterus based on the amount of the 4 metabolites in the sample of culture media, wherein: i) the amount of at least one of the metabolites in the sample of culture media is associated with a low probability of embryo implantation success; and ii) the amount of at least one of the metabolites in the sample of culture media is associated with a high probability of implantation success.

Embodiment 68. The method of embodiment 67, wherein one of the metabolites is caprolactam.

Embodiment 69. The method of embodiment 67 or 68, wherein one of the metabolites is N-cyclohexylformamide.

Embodiment 70. The method of any one of embodiments 67-69, wherein one of the metabolites is threo-3-hydroxy-2-methylbutyric acid.

Embodiment 71. The method of any one of embodiments 67-70, wherein one of the metabolites is sulfoacetic acid.

Embodiment 72. The method of any one of embodiments 67-71, wherein one of the metabolites is (2,7-dimethyloctahydro-1H-cyclopenta[c]pyridin-4-yl)methanol.

Embodiment 73. The method of any one of embodiments 67-72, wherein one of the metabolites is trans-3-indoleacrylic acid.

Embodiment 74. The method of any one of embodiments 67-73, wherein one of the metabolites is pantothenic acid.

Embodiment 75. The method of any one of embodiments 67-74, wherein one of the metabolites is diaveridine.

Embodiment 76. The method of any one of embodiments 67-75, wherein one of the metabolites is (5-benzyl-3,6-dioxo-2-piperazinyl)acetic acid.

Embodiment 77. The method of any one of embodiments 67-76, wherein one of the metabolites is dasytrichone.

Embodiment 78. The method of any one of embodiments 67-77, wherein one of the metabolites is indole.

Embodiment 79. The method of any one of embodiments 67-78, wherein one of the metabolites is leucoline.

Embodiment 80. The method of any one of embodiments 67-79, wherein one of the metabolites is skatole.

Embodiment 81. The method of any one of embodiments 67-80, wherein one of the metabolites is 6-hydroxycaproic acid.

Embodiment 82. The method of any one of embodiments 67-81, wherein one of the metabolites is 1,2,6-hexanetriol.

Embodiment 83. The method of any one of embodiments 67-82, wherein one of the metabolites is naphthalen-2-amine.

Embodiment 84. The method of any one of embodiments 67-83, wherein one of the metabolites is 8-hydroxyquinoline.

Embodiment 85. The method of any one of embodiments 67-84, wherein one of the metabolites is 2,2,6,6-tetramethyl-4-piperidinol.

Embodiment 86. The method of any one of embodiments 67-85, wherein one of the metabolites is 1,5-naphthalenediamine.

Embodiment 87. The method of any one of embodiments 67-86, wherein one of the metabolites is 1H-indole-2-carboxylic acid.

Embodiment 88. The method of any one of embodiments 67-87, wherein one of the metabolites is (E)-dacarbazine.

Embodiment 89. The method of any one of embodiments 67-88, wherein one of the metabolites is dinitrosopentamethylenetetramine.

Embodiment 90. The method of any one of embodiments 67-89, wherein one of the metabolites is 5-hydroxyindole-3-acetic acid.

Embodiment 91. The method of any one of embodiments 67-90, wherein one of the metabolites is 3-amino-5,7-dimethyl-1-adamantanol.

Embodiment 92. The method of any one of embodiments 67-91, wherein one of the metabolites is 11-aminoundecanoic acid.

Embodiment 93. The method of any one of embodiments 67-92, wherein one of the metabolites is kynurenine.

Embodiment 94. The method of any one of embodiments 67-93, wherein one of the metabolites is N-hydroxy-L-tryptophan.

Embodiment 95. The method of any one of embodiments 67-94, wherein one of the metabolites is 2-(methylamino)-1H-benzo[de]isoquinoline-1,3(2H)-dione.

Embodiment 96. The method of any one of embodiments 67-95, wherein one of the metabolites is 5-hydroxy-N-formylkynurenine.

Embodiment 97. The method of any one of embodiments 67-96, wherein one of the metabolites is N-lauroylglycine.

Embodiment 98. The method of any one of embodiments 67-97, wherein one of the metabolites is DL-tryptophan.

Embodiment 99. The method of any one of embodiments 67-98, wherein one of the metabolites is phenylalanine.

Embodiment 100. A method comprising: a) requesting an assay on a sample of culture media in which an embryo has been cultured in vitro, b) receiving a communication, wherein the communication assesses a likelihood of success of implantation of the embryo into a uterus upon introduction of the embryo into the uterus based on an amount of one or more metabolites measured in the sample of culture media; and c) transferring the embryo into a subject's uterus, wherein: i) the communication states that the likelihood of success of implantation of the embryo into the uterus is high; and ii) one of the metabolites measured in the sample of culture media is caprolactam, N-cyclohexylformamide, threo-3-hydroxy-2-methylbutyric acid, sulfoacetic acid, (2,7-dimethyloctahydro-1H-cyclopenta[c]pyridin-4-yl) methanol, trans-3-indoleacrylic acid, pantothenic acid, diaveridine, (5-benzyl-3,6-dioxo-2-piperazinyl)acetic acid, dasytrichone, indole, leucoline, skatole, 6-hydroxycaproic acid, 1,2,6-hexanetriol, naphthalen-2-amine, 8-hydroxyquinoline, 2,2,6,6-tetramethyl-4-piperidinol, 1,5-naphthalenediamine, 1H-indole-2-carboxylic acid, (E)-dacarbazine, dinitrosopentamethylenetetramine, 5-hydroxyindole-3-acetic acid, 3-amino-5,7-dimethyl-1-adamantanol, 11-aminoundecanoic acid, kynurenine, N-hydroxy-L-tryptophan, 2-(methylamino)-1H-benzo[de]isoquinoline-1,3(2H)-dione, 5-hydroxy-N-formylkynurenine, or N-lauroylglycine.

Embodiment 101. The method of embodiment 100, wherein the likelihood of success of implantation of the embryo is based on the amount of caprolactam measured in the sample of culture media.

Embodiment 102. The method of embodiment 100, wherein the likelihood of success of implantation of the embryo is based on the amount of N-cyclohexylformamide measured in the sample of culture media.

Embodiment 103. The method of embodiment 100, wherein the likelihood of success of implantation of the embryo is based on the amount of threo-3-hydroxy-2-methylbutyric acid measured in the sample of culture media.

Embodiment 104. The method of embodiment 100, wherein the likelihood of success of implantation of the embryo is based on the amount of sulfoacetic acid measured in the sample of culture media Embodiment 105. The method of embodiment 100, wherein the likelihood of success of implantation of the embryo is based on the amount of (2,7-dimethyloctahydro-1H-cyclopenta[c]pyridin-4-yl)methanol measured in the sample of culture media.

Embodiment 106. The method of embodiment 100, wherein the likelihood of success of implantation of the embryo is based on the amount of trans-3-indoleacrylic acid measured in the sample of culture media.

Embodiment 107. The method of embodiment 100, wherein the likelihood of success of implantation of the embryo is based on the amount of pantothenic acid measured in the sample of culture media.

Embodiment 108. The method of embodiment 100, wherein the likelihood of success of implantation of the embryo is based on the amount of diaveridine measured in the sample of culture media.

Embodiment 109. The method of embodiment 100, wherein the likelihood of success of implantation of the embryo is based on the amount of (5-benzyl-3,6-dioxo-2-piperazinyl)acetic acid measured in the sample of culture media.

Embodiment 110. The method of embodiment 100, wherein the likelihood of success of implantation of the embryo is based on the amount of dasytrichone measured in the sample of culture media.

Embodiment 111. The method of embodiment 100, wherein the likelihood of success of implantation of the embryo is based on the amount of indole measured in the sample of culture media.

Embodiment 112. The method of embodiment 100, wherein the likelihood of success of implantation of the embryo is based on the amount of leucoline measured in the sample of culture media.

Embodiment 113. The method of embodiment 100, wherein the likelihood of success of implantation of the embryo is based on the amount of skatole measured in the sample of culture media.

Embodiment 114. The method of embodiment 100, wherein the likelihood of success of implantation of the embryo is based on the amount of 6-hydroxycaproic acid measured in the sample of culture media.

Embodiment 115. The method of embodiment 100, wherein the likelihood of success of implantation of the embryo is based on the amount of 1,2,6-hexanetriol measured in the sample of culture media.

Embodiment 116. The method of embodiment 100, wherein the likelihood of success of implantation of the embryo is based on the amount of naphthalen-2-amine measured in the sample of culture media.

Embodiment 117. The method of embodiment 100, wherein the likelihood of success of implantation of the embryo is based on the amount of 8-hydroxyquinoline measured in the sample of culture media.

Embodiment 118. The method of embodiment 100, wherein the likelihood of success of implantation of the embryo is based on the amount of 2,2,6,6-tetramethyl-4-piperidinol measured in the sample of culture media.

Embodiment 119. The method of embodiment 100, wherein the likelihood of success of implantation of the embryo is based on the amount of 1,5-naphthalenediamine measured in the sample of culture media.

Embodiment 120. The method of embodiment 100, wherein the likelihood of success of implantation of the embryo is based on the amount of 1H-indole-2-carboxylic acid measured in the sample of culture media.

Embodiment 121. The method of embodiment 100, wherein the likelihood of success of implantation of the embryo is based on the amount of (E)-dacarbazine measured in the sample of culture media.

Embodiment 122. The method of embodiment 100, wherein the likelihood of success of implantation of the embryo is based on the amount of dinitrosopentamethylenetetramine measured in the sample of culture media.

Embodiment 123. The method of embodiment 100, wherein the likelihood of success of implantation of the embryo is based on the amount of 5-hydroxyindole-3-acetic acid measured in the sample of culture media.

Embodiment 124. The method of embodiment 100, wherein the likelihood of success of implantation of the embryo is based on the amount of 3-amino-5,7-dimethyl-1-adamantanol measured in the sample of culture media.

Embodiment 125. The method of embodiment 100, wherein the likelihood of success of implantation of the embryo is based on the amount of 11-aminoundecanoic acid measured in the sample of culture media.

Embodiment 126. The method of embodiment 100, wherein the likelihood of success of implantation of the embryo is based on the amount of kynurenine measured in the sample of culture media.

Embodiment 127. The method of embodiment 100, wherein the likelihood of success of implantation of the embryo is based on the amount of N-hydroxy-L-tryptophan measured in the sample of culture media.

Embodiment 128. The method of embodiment 100, wherein the likelihood of success of implantation of the embryo is based on the amount of 2-(methylamino)-1H-benzo[de]isoquinoline-1,3(2H)-dione measured in the sample of culture media.

Embodiment 129. The method of embodiment 100, wherein the likelihood of success of implantation of the embryo is based on the amount of 5-hydroxy-N-formylkynurenine measured in the sample of culture media.

Embodiment 130. The method of embodiment 100, wherein the likelihood of success of implantation of the embryo is based on the amount of N-lauroylglycine measured in the sample of culture media.

Embodiment 131. A kit comprising an aliquot of each of 3 of the following compounds: caprolactam, N-cyclohexylformamide, threo-3-hydroxy-2-methylbutyric acid, sulfoacetic acid, (2,7-dimethyloctahydro-1H-cyclopenta[c]pyridin-4-yl)methanol, trans-3-indoleacrylic acid, pantothenic acid, diaveridine, (5-benzyl-3,6-dioxo-2-piperazinyl)acetic acid, dasytrichone, indole, leucoline, skatole, 6-hydroxycaproic acid, 1,2,6-hexanetriol, naphthalen-2-amine, 8-hydroxyquinoline, 2,2,6,6-tetramethyl-4-piperidinol, 1,5-naphthalenediamine, 1H-indole-2-carboxylic acid, (E)-dacarbazine, dinitrosopentamethylenetetramine, 5-hydroxyindole-3-acetic acid, 3-amino-5,7-dimethyl-1-adamantanol, 11-aminoundecanoic acid, kynurenine, N-hydroxy-L-tryptophan, 2-(methylamino)-1H-benzo[de]isoquinoline-1,3(2H)-dione, 5-hydroxy-N-formylkynurenine, DL-tryptophan, phenylalanine, and N-lauroylglycine.

What is claimed is:

1. A method comprising:
    a) obtaining a sample of culture media in which an embryo has been cultured in vitro;
    b) i) measuring from the sample an amount of one or more non-pregnancy metabolites associated with a low probability of embryo implantation success,
    wherein at least one of the non-pregnancy metabolites is indole, leucoline, skatole, 6-hydroxycaproic acid, 1,2, 6-hexanetriol, naphthalen-2-amine, 8-hydroxyquinoline, 2,2,6,6-tetramethyl-4-piperidinol, 1,5-naphthalenediamine, 1H-indole-2-carboxylic acid, (E)-dacarbazine, dinitrosopentamethylenetetramine, 5-hydroxyindole-3-acetic acid, 3-amino-5,7-dimethyl-1-adamantanol, 11-aminoundecanoic acid, kynurenine, N-hydroxy-L-tryptophan, 2-(methylamino)-1H-benzo[de]isoquinoline-1,3 (2H)-dione, 5-hydroxy-N-formylkynurenine, or N-lauroylglycine;
    b) ii) measuring from the sample an amount of one or more pregnancy metabolites associated with a high probability of implantation success,
    wherein at least one of the pregnancy metabolites is caprolactam, N-cyclohexylformamide, threo-3-Hydroxy-2-methylbutyric acid, sulfoacetic acid, phenylalanine, (2,7-Dimethyloctahydro-1H-cyclopenta[c]pyridin-4-yl)methanol, trans-3-indoleacrylic acid, DL-tryptophan, pantothenic acid, diaveridine, (5-benzyl-3,6-dioxo-2-piperazinyl)acetic acid, or dasytrichone;
c) comparing the amount of the one or more non-pregnancy metabolites and the amount of the one or more pregnancy metabolites; and
d) transferring the one or more embryos with a high probability of implantation success based on step c) into a subject's uterus.

2. The method of claim 1, wherein one of the pregnancy metabolites is caprolactam.

3. The method of claim 1, wherein one of the pregnancy metabolites is N-cyclohexylformamide.

4. The method of claim 1, wherein one of the pregnancy metabolites is threo-3-hydroxy-2-methylbutyric acid.

5. The method of claim 1, wherein one of the pregnancy metabolites is sulfoacetic acid.

6. The method of claim 1, wherein one of the pregnancy metabolites is (2,7-dimethyloctahydro-1H-cyclopenta[c]pyridin-4-yl)methanol.

7. The method of claim 1, comprising measuring the pregnancy metabolite trans-3-indoleacrylic acid.

8. The method of claim 1, wherein one of the pregnancy metabolites is pantothenic acid.

9. The method of claim 1, wherein one of the pregnancy metabolites is diaveridine.

10. The method of claim 1, wherein one of the pregnancy metabolites is (5-benzyl-3,6-dioxo-2-piperazinyl)acetic acid.

11. The method of claim 1, wherein one of the pregnancy metabolites is dasytrichone.

12. The method of claim 1, comprising measuring the non-pregnancy metabolite indole.

13. The method of claim 1, wherein one of the non-pregnancy metabolites is leucoline.

14. The method of claim 1, comprising measuring the non-pregnancy metabolite skatole.

15. The method of claim 1, wherein one of the non-pregnancy metabolites is 6-hydroxycaproic acid.

16. The method of claim 1, wherein one of the non-pregnancy metabolites is 1,2,6-hexanetriol.

17. The method of claim 1, wherein one of the non-pregnancy metabolites is naphthalen-2-amine.

18. The method of claim 1, wherein one of the non-pregnancy metabolites is 8-hydroxyquinoline.

19. The method of claim 1, wherein one of the non-pregnancy metabolites is 2,2,6,6-tetramethyl-4-piperidinol.

20. The method of claim 1, wherein one of the non-pregnancy metabolites is 1,5-naphthalenediamine.

21. The method of claim 1, wherein one of the non-pregnancy metabolites is 1H-indole-2-carboxylic acid.

22. The method of claim 1, wherein one of the non-pregnancy metabolites is (E)-dacarbazine.

23. The method of claim 1, wherein one of the non-pregnancy metabolites is dinitrosopentamethylenetetramine.

24. The method of claim 1, wherein one of the non-pregnancy metabolites is 5-hydroxyindole-3-acetic acid.

25. The method of claim 1, wherein one of the non-pregnancy metabolites is 3-amino-5,7-dimethyl-1-adamantanol.

26. The method of claim 1, wherein one of the non-pregnancy metabolites is 11-aminoundecanoic acid.

27. The method of claim 1, wherein one of the non-pregnancy metabolites is kynurenine.

28. The method of claim 1, wherein one of the non-pregnancy metabolites is N-hydroxy-L-tryptophan.

29. The method of claim 1, wherein one of the non-pregnancy metabolites is 2-(methylamino)-1H-benzo[de]isoquinoline-1,3 (2H)-dione.

30. The method of claim 1, wherein one of the non-pregnancy metabolites is 5-hydroxy-N-formylkynurenine.

31. The method of claim 1, wherein one of the non-pregnancy metabolites is N-lauroylglycine.

32. The method of claim 1, comprising measuring the pregnancy metabolite DL-tryptophan.

33. The method of claim 1, wherein one of the pregnancy metabolites is phenylalanine.

34. The method of claim 1, comprising measuring more than one non-pregnancy metabolite and measuring more than one pregnancy metabolite.

35. The method of claim 34, wherein
step b) i) comprises measuring each of the non-pregnancy metabolites: indole, leucoline, skatole, 8-hydroxyquinoline, 2,2,6,6-tetramethyl-4-piperidinol, 1,5-naphthalenediamine, 3-amino-5,7-dimethyl-1-adamantanol, 11-aminoundecanoic acid, N-hydroxy-L-tryptophan, and N-lauroylglycine; and
step b) ii) comprises measuring each of the pregnancy metabolites: caprolactam, phenylalanine, (2,7-Dimethyloctahydro-1H-cyclopenta[c]pyridin-4-yl)methanol, trans-3-indoleacrylic acid, DL-tryptophan, pantothenic acid, diaveridine, and (5-benzyl-3,6-dioxo-2-piperazinyl)acetic acid.

36. The method of claim 1, wherein the measuring steps comprise a mass spectrometry (MS)-based approach.

37. The method of claim 36, wherein the mass spectrometry (MS)-based approach comprises Fourier transform ion cyctrotron resonance-mass spectrometry (FTICR-MS), Fusion Orbitrap MS, UPLC-coupled Fusion Orbitrap MS, collision-dissociation-tandem MS (CID-MS/MS), higher-energy collision dissociation-coupled tandem MS (HCD-MS/MS), infrared multiphoton dissociation-tandem MS (IRMPD-MS/MS), liquid chromatography triple quadrupole tandem mass spectrometry (LC-QqQ-MS), GC-MS, LC-MS, IC-MS, or capillary electrophoresis-MS (CE-MS).

38. The method of claim 1, wherein the sample of culture media is obtained after an embryo has been cultured in vitro for 0.05 to 8 days.

39. The method of claim 37, wherein step c) comprises calculating a Metabolite Pregnancy Index (MPI) by dividing the total integrated area of mass spectra peaks corresponding to the pregnancy metabolites by the total integrated area of mass spectra peaks corresponding to the non-pregnancy metabolites.

40. The method of claim 39, wherein step d) comprises selecting at least one embryo with an MPI greater than 1.0.

41. The method of claim 40, wherein step d) comprises selecting at least one embryo with an MPI greater than 5.

42. The method of claim 41, wherein step d) comprises selecting at least one embryo with an MPI greater than 10.

43. A method comprising:
a) obtaining a sample of culture media in which an embryo has been cultured in vitro;
b) i) measuring from the sample an amount of one or more non-pregnancy metabolites associated with a low probability of embryo implantation success,
wherein at least one of the non-pregnancy metabolites is indole, leucoline, skatole, 6-hydroxycaproic acid, 1,2, 6-hexanetriol, naphthalen-2-amine, 8-hydroxyquinoline, 2,2,6,6-tetramethyl-4-piperidinol, 1,5-naphthalenediamine, 1H-indole-2-carboxylic acid, (E)- dacarbazine, dinitrosopentamethylenetetramine, 5-hydroxyindole-3-acetic acid, 3-amino-5,7-dimethyl-1-adamantanol, 11-aminoundecanoic acid, N-hydroxy-L-tryptophan, 2-(methylamino)-1H-benzo[de]isoquinoline-1,3 (2H)-dione, 5-hydroxy-N-formylkynurenine, or N-lauroylglycine;

b) ii) measuring from the sample an amount of one or more pregnancy metabolites associated with a high probability of implantation success, wherein at least one of the pregnancy metabolites is caprolactam, N-cyclohexylformamide, threo-3-Hydroxy-2-methylbutyric acid, sulfoacetic acid, phenylalanine, (2,7-Dimethyloctahydro-1H-cyclopenta[c]pyridin-4-yl)methanol, trans-3-indoleacrylic acid, DL-tryptophan, pantothenic acid, diaveridine, (5-benzyl-3,6-dioxo-2-piperazinyl)acetic acid, or dasytrichone;

c) comparing the amount of the one or more non-pregnancy metabolites and the amount of the one or more pregnancy metabolites; and d) transferring the one or more embryos with a high probability of implantation success based on step c) into a subject's uterus.

44. A method comprising:

a) obtaining a sample of culture media in which an embryo has been cultured in vitro;

b) i) measuring from the sample an amount of one or more non-pregnancy metabolites associated with a low probability of embryo implantation success, wherein at least one of the non-pregnancy metabolites exhibits a molecular weight of about: 117.06, 129.06, 131.07, 132.08, 134.09, 143.07, 145.05, 157.15, 158.08, 161.05, 182.09, 186.09, 191.06, 195.16, 201.17, 208.08, 220.08, 226.07, 252.07, or 257.20;

b) ii) measuring from the sample an amount of one or more pregnancy metabolites associated with a high probability of implantation success, wherein at least one of the pregnancy metabolites exhibits a molecular weight of about: 113.08, 127.10, 132.08, 139.94, 165.08, 183.16, 187.06, 204.09, 219.11, 260.12, 262.09, or 296.10;

c) comparing the amount of the one or more non-pregnancy metabolites and the amount of the one or more pregnancy metabolites; and d) transferring the one or more embryos with a high probability of implantation success based on step c) into a subject's uterus.

\* \* \* \* \*